(12) United States Patent
Gardner

(10) Patent No.: US 7,214,942 B2
(45) Date of Patent: May 8, 2007

(54) GAMMA RAY DETECTORS HAVING IMPROVED SIGNAL-TO-NOISE RATIO AND RELATED SYSTEMS AND METHODS FOR ANALYZING BULK MATERIALS

(75) Inventor: Robin Pierce Gardner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 238 days.

(21) Appl. No.: 10/820,633

(22) Filed: Apr. 8, 2004

(65) Prior Publication Data

US 2004/0256566 A1    Dec. 23, 2004

Related U.S. Application Data

(60) Provisional application No. 60/461,801, filed on Apr. 10, 2003.

(51) Int. Cl.
G01N 23/22    (2006.01)
(52) U.S. Cl. .................................... 250/360.1
(58) Field of Classification Search .............. 250/360.1
See application file for complete search history.

(56) References Cited

U.S. PATENT DOCUMENTS

| | | | |
|---|---|---|---|
| 2,830,184 A | 4/1958 | Scherbatskoy | 250/71 |
| 2,881,324 A | 4/1959 | Scherbatskoy | 250/71 |
| 2,946,888 A | 7/1960 | Scherbatskoy | 250/71.5 |
| 2,992,331 A | 7/1961 | Bonner et al. | 250/71.5 |
| 3,041,454 A | 6/1962 | Jones et al. | 250/71.5 |
| 3,041,455 A | 6/1962 | Meyerhof | 250/71.5 |
| 3,088,030 A | 4/1963 | Rickard | 250/71.5 |
| 3,626,187 A * | 12/1971 | Laney | 250/362 |
| 3,654,464 A | 4/1972 | Johnson, Jr. et al. | 250/71.5 |

(Continued)

FOREIGN PATENT DOCUMENTS

GB    1000044    8/1965

OTHER PUBLICATIONS

Bartholomew et al., "The $^{199}$Hg $(n, \gamma)$ $^{200}$Hg Reaction With Thermal Neutrons," *Canadian Journal of Physics* 45:1517-1540 (1967).

(Continued)

*Primary Examiner*—Constantine Hannaher
(74) *Attorney, Agent, or Firm*—Myers Bigel Sibley & Sajovec

(57) ABSTRACT

An assembly for detecting gamma rays from a bulk material defines a radiation region. A radiation source is positioned adjacent the radiation region and configured to irradiate the bulk material in the radiation region. A first gamma ray detector is positioned adjacent a side of the radiation region and is configured to detect gamma ray events including events from gamma rays secondarily emitted by the bulk material responsive to radiation from the radiation source. A second gamma ray detector is positioned adjacent the first gamma ray detector and configured to detect gamma ray events including events from gamma rays secondarily emitted by the bulk material responsive to radiation from the radiation source. A coincidence module is configured to receive signals indicating gamma ray events from the first and second gamma ray detectors and to identify events that are detected in coincidence in the first and the second gamma ray detectors.

21 Claims, 39 Drawing Sheets

U.S. PATENT DOCUMENTS

| | | | | |
|---|---|---|---|---|
| 4,582,991 | A | * | 4/1986 | Atwell et al. ............. 250/359.1 |
| 4,764,677 | A | | 8/1988 | Spurney ...................... 250/361 |
| 4,841,153 | A | * | 6/1989 | Wormald ............... 250/390.04 |
| 4,937,446 | A | | 6/1990 | McKeon et al. ............ 280/270 |
| 2004/0256548 | A1 | | 12/2004 | Gardner ...................... 250/266 |

OTHER PUBLICATIONS

Bartholomew et al., "Spins of Levels in $N^{15}$, $Fe^{57}$, $Cu^{64}$, $Zr^{92}$, and $Hg^{200}$ by Neutron Capture $\gamma$-Ray Directional Correlations," *Nuclear Physics* 50:209-233 (1964).

Hoogerboom, A.M., "A New Method In Gamma-Ray Spectroscopy: A Two Crystal Scintillation Spectrometer With Improved Resolution," *Nuclear* Instruments 3:57-68 (1958).

International Search Report for PCT/US2004/011665; Date of mailing Nov. 11, 2004, not a publication.

Ember et al. "Improvement of the capabilities of PGAA by coincidence techniques", Applied Radiation and Isotopes 56:535-541 (2002).

Ember et al. "Coincidence measurement setup for PGAA and nuclear structure studies", Applied Radiation and Isotopes 57:573-577 (2002).

International Search Report for PCT/US2004/011666; Date of mailing Dec. 29, 2004.

International Search Report and Written Opinion of the International Searching Authority for Application No. PCT/US2004/011666 mailed on Apr. 28, 2005, not a publication.

Gardner et al., "A feasibility study of a coincidence counting approach for PGNAA applications", Applied Radiation and Isotopes 53 (2000) 515-526.

Gardner et al., "Practical Implementation of Coincidence Prompt Gamma-Ray Neutron Activation Analysis", Transactions of the American Nuclear Society, vol. 89, pp. 486-487, 2003.

Metwally et al., "Elemental PGNAA analysis using gamma-gamma coincidence counting with the library least squares approach," Nuclear Instruments and Methods in Physics Research B 213 (2004) 394-399.

Metwally et al., "Two-dimensional diagonal summering of coincidence spectra for bulk PGNAA applications, " Nuclear Instruments and Methods in Physics Research A 525 (2004) 511-517.

Gardner et al., "Q-value Summing for Coincidence Prompt Gamma-Ray Neutron Activation Analysis," Transactions of the American Nuclear Society, vol. 91, pp. 881-882, 2004.

Gardner et al., A new NaI detector arrangement for efficient detection of high energy gamma-rays, Journal of Radioanalytical and Nuclear Chemistry, vol. 264, No. 1 (2005) 133-137.

Metwally et al. "Coincidence counting for PGNAA applications: Is it the optimum method?" Journal of Radioanalytical and Nuclear Chemistry, vol. 265, No. 2 (2005) 309-314.

\* cited by examiner

GAMMA RAY DETECTORS HAVING IMPROVED SIGNAL-TO-NOISE RATIO AND RELATED SYSTEMS AND METHODS FOR ANALYZING BULK MATERIALS

RELATED APPLICATIONS

This application claims the benefit of priority to U.S. Provisional Application Ser. No. 60/461,801, entitled, "Gamma Ray Detectors Having Improved Signal to Noise Ratio And Related Systems And Methods" filed Apr. 10, 2003, the disclosure of which is hereby herein incorporated by reference in its entirety.

FIELD OF THE INVENTION

The present invention relates generally to the analysis of bulk materials using gamma rays, for example, from neutron activation and, more particularly, to detectors having improved signal-to-noise ratio for analysis of gamma rays and related methods.

BACKGROUND OF THE INVENTION

The composition of a bulk material can be analyzed based on the characteristics of the gamma rays detected by a gamma ray detector. For example, elements typically emit gamma rays at certain characteristic energies when activated with a suitable source of neutrons during neutron activation. These techniques have been used to analyze bulk materials, for example, to determine the sulfur content of coal using gamma ray detection during neutron activation.

High sulfur levels in coal are generally bad for the environment. The sulfur content of coal may be analyzed by detecting gamma rays emitted from sulfur during neutron activation. The sulfur content of coal may be used to comply with environmental regulations. Bulk material analyzers generally include a fast neutron source and a radiation detector spaced apart from the source. The fast neutrons originating from the source collide with elements in the bulk material. The neutrons may collide with elements with small nuclei, such as hydrogen or carbon, and be slowed by elastic scattering, or these collisions can result in the emission of inelastic gamma rays, which subsequently can result in the slowing down of the neutrons. Upon slowing down, the neutrons may be captured with higher probability and another set of gamma rays may be emitted. The resulting gamma rays, either before or after neutron slowing, are detected by the radiation detectors and the resulting spectra are analyzed to obtain information about the elemental amounts in the bulk material.

SUMMARY

According to embodiments of the present invention, an assembly for detecting gamma rays from a bulk material is provided. The assembly defines a radiation region. A radiation source is positioned adjacent the radiation region and is configured to irradiate the bulk material in the radiation region. A first gamma ray detector is positioned adjacent the radiation region and is configured to detect gamma ray events including events from gamma rays secondarily emitted by the bulk material responsive to radiation from the radiation source. A second gamma ray detector is positioned adjacent the first gamma ray detector and is configured to detect gamma ray events including events from gamma rays secondarily emitted by the bulk material responsive to radiation from the radiation source. A coincidence module is configured to receive signals indicating gamma ray events from the first and second gamma ray detectors and to identify events that are detected in coincidence in the first and the second gamma ray detectors.

In this configuration, particular interactions and/or energy levels can be identified based on the detection of coincidence events and the signal-to-noise ratio can be improved.

In some embodiments, a first photomultiplier tube is in communication with the first gamma ray detector and a second photomultiplier tube is in communication with the second gamma ray detector. In other embodiments, the second gamma ray detector includes an array of gamma ray detectors such that each of the gamma ray detectors in the array is configured to provide respective signals indicating gamma ray events.

In particular embodiments, the signal processor is configured to determine coincidence counting rates between the first and second gamma ray detectors. The coincidence counting rate can be the total rate of coincidence between the first and second gamma ray detectors. The signal processor may be configured to select a subset of the events from one of the first and/or second detectors and to identify gamma ray events in the other of the first and/or second detectors in coincidence with the selected subset. The coincidence counting rate can be the rate of coincidence between a first event and a second event such that the first event and the second event sum to a predetermined energy. According to some embodiments, the predetermined energy is between about 1.5 MeV to about 11 MeV.

In some embodiments, the processor can be configured to generate a two-dimensional plot based on the signals from the first and second gamma ray detectors and/or to generate a one-dimensional diagonal summation plot based on the two-dimensional plot.

In some embodiments, the assembly includes a conveyor belt configured to transport the bulk material through the radiation region. In other embodiments, the assembly includes a chute configured to continually transport the bulk material through the radiation region.

In further embodiments of the invention, methods of detecting coincidence in gamma ray detectors for analyzing a bulk material are provided. The bulk material is provided in a radiation region and irradiated in the radiation region with a radiation source adjacent the radiation region. Gamma ray events are detected with a first gamma ray detector adjacent the radiation region. Gamma ray events are detected with a second gamma ray detector adjacent the first gamma ray detector. The gamma ray events include events from gamma rays secondarily emitted by the bulk material responsive to radiation from the radiation source. Gamma ray events are identified that are detected in coincidence in the first and the second gamma ray detectors.

Coincidence counting techniques according to embodiments of the present invention may be made of entirely hardware, entirely software, or a combination of hardware and software embodiments.

DETAILED DESCRIPTION OF EMBODIMENTS OF THE INVENTION

Figure 1:
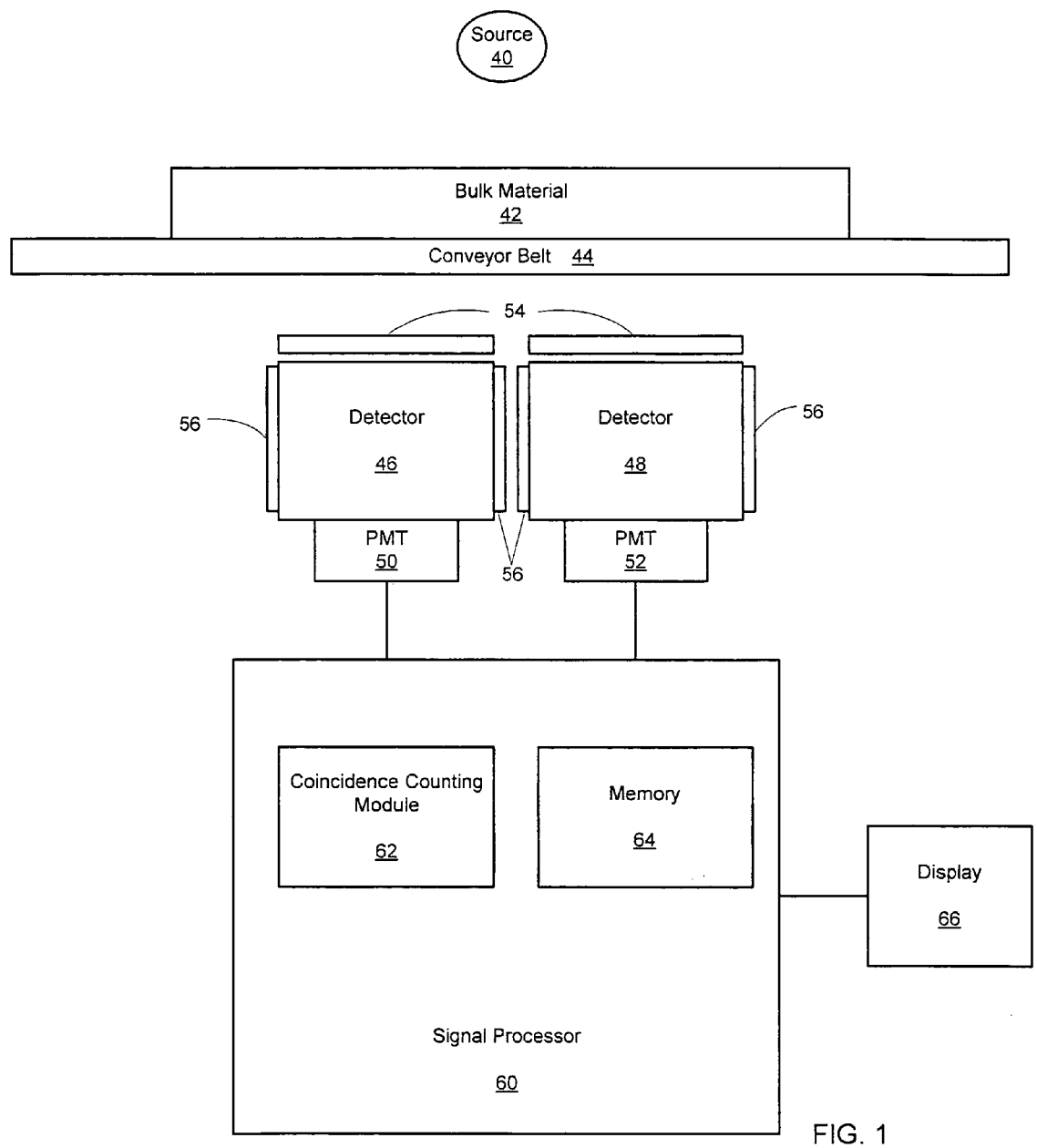
FIG. 1 is a schematic diagram of a gamma ray detector assembly and a conveyor belt positioned to provide analysis of a bulk material and a data processor according to embodiments of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements throughout. Thicknesses and dimensions of some components may not be drawn to scale and may be exaggerated for clarity. It will be understood that when an element is referred to as being "on" or "adjacent" another element, it can be directly on or adjacent the other element or intervening elements may also be present. In contrast, when an element is referred to as being "directly on" another element, there are no intervening elements present.

As used herein, the term "event" refers to the detection of a gamma ray or gamma ray interaction. Two or more events may be caused by the same gamma ray.

FIG. 1 illustrates embodiments of the invention that may be used to analyze a bulk material 42. The bulk material 42 can be placed between a source 40 and detectors 46, 48. In this configuration, interactions between particles, such as neutrons emitted from the source 40 and the bulk material 42, can be detected in the detectors 46, 48. As illustrated, the bulk material 42 can be moved along a conveyor belt 44 past the detectors 46, 48 to increase the amount of material that can be analyzed. Alternatively, the bulk material 42 could be stationary or could be moved by other techniques, such as being passed down a chute or slide at an angle.

As shown in FIG. 1, the detectors 46, 48 are scintillation detectors connected to photomultiplier tubes 50, 52. The detectors 46, 48 are used to detect gamma rays produced as a result of interactions between neutrons from the source 40 and the bulk material 42. The detectors 46, 48 may be surrounded by a gamma ray shielding material 56, such as lead, and covered with a neutron shielding sheet 54. For example, a lithium sheet may be used for shielding sheet 54; however, boron and gadolinium may also be used. The shielding sheet 54 can be suitably sized and configured to shield the detectors 46, 48 from thermal neutrons that could otherwise damage or activate the detectors 46, 48.

In this configuration, bulk material can be analyzed using gamma rays, for example, from neutron activation. Embodiments of the present invention can incorporate coincidence-counting techniques that may improve the signal-to-noise ratio and reduce background in a dataset or spectrum. The effects of summing and pulse pile up may also be reduced. "Summing" and "pulse pile up" refer to coincidence events that are detected at substantially the same time in one detector. This results in two or more events being detected as a single event having a detected energy equal to as much as the sum of the energies of the coincidence events. "Summing" or a "sum peak" in the resulting spectrum is generally the result of gamma rays emitted from a source at the same time in coincidence. "Pulse pile up" generally refers to random coincidence events from more than one source.

The source 40 can be any suitable source, such as fast neutron source, including an accelerator source that produces neutrons with an energy of about 14 MeV. The source 40 can be placed over a layer of wax (not shown) to thermalize fast neutrons from the source. Examples of neutron sources include Cf-252, Am-241-Be, and radium/beryllium sources. Without wishing to be bound by theory, the collisions between neutrons from the source 40 and the bulk material 42 may result in eelastic interactions that slow the neutrons or in the emission of inelastic gamma rays and, subsequently, the slowing down of the neutrons. Upon slowing down, the neutrons may be captured with higher probability, which may emit still more gamma rays. The gamma rays from these and other reactions may be detected by the detectors 46, 48 and the photomultiplier tubes 50, 52.

Signals indicating the detection of events in the detectors 46, 48 are processed by the signal processor 60. The signal processor 60 includes a coincidence counting module 62 and memory 64 connected to a display 66.

Gamma rays are generally detected when an incident gamma ray interacts with matter in a detector. Such events may be detected in two or more detectors in "coincidence." That is, when two or more events occur within a certain time range, typically between about 10 to about 100 nanoseconds or less, the events can be defined as being in coincidence.

Any suitable detector can be used for the detectors 46, 48. For example, the detectors 46, 48 may be scintillating radiation detectors such as scintillating detectors including crystals such as NaI(Tl), BGO, KBr(Tl), NaBr(Tl), KI(Tl), KCl(Tl), CsI(Na), CsI(Tl) or polyvinyl toluene plastic scintillators. Scintillating radiation detectors typically utilize a photomultiplier tube to detect scintillation and amplify the resulting signal. The detectors 46, 48 may also be semiconductor detectors such as germanium, Si(Li) or gallium nitride detectors. Such detectors may not require photomultiplier tubes 50, 52, and therefore, the photomultiplier tubes 50, 52 may be omitted. A "gamma camera" can also be used. Gamma cameras are commercially available from General Electric Medical Systems (Waukesha, Milwalkee, U.S.A.). In some embodiments, a coincidence device such as a Sparrow™ system may be used (commercially available from Sparrow Corporation in Port Orange, Fla., U.S.A.). A Sparrow™ system is capable of recording individual spectral counting rates from each of the detectors 46, 48 while also recording the coincidence counting rates that occur at specific energies in each of the detectors 46, 48. This latter data may be three-dimensional or two-dimensional and can provide the counts or counting rate as a function of the energy deposited in one detector and energy that is deposited in a second detector in coincidence. From this three-dimensional data (e.g., event counts as a function of energy in one detector and event counts as a function of energy in another detector), those pulses that satisfy a predetermined coincidence criteria, such as events adding to a prescribed energy or events in one detector that are in coincidence with a prescribed energy range in the other detector, can be extracted.

The signal processor 60 can process signals indicative of events detected by the detectors 46, 48. The coincidence counting module 62 can determine a coincidence counting rate by identifying if events are in coincidence, and coincidence, anti-coincidence, and/or single events can be recorded or stored in the memory 64. For example, signal processing may occur in real time, or data may be stored in the memory 64. Although the coincidence counting module 62 is illustrated with respect to the signal processor 60, other configurations can be used. For example, the coincidence counting module 62 can be provided as part of an integrated detector assembly. The coincidence counting module 62 can carry out operations according to embodiments of the present invention such as reading data from the memory 64 or from the detectors 46, 48 in order to determine if events are coincidence events or if an event is a single event.

In this configuration, the composition of the bulk material 42 may be analyzed. For example, the bulk material 42 can be coal, and the sulfur and/or ash content of the coal can be determined. As another example, the bulk material 42 can be a cement mixture.

The display 66 can display raw data and/or data that has been processed by the signal processor 60. The display 66 may be part of the signal processor 60 or a separate device. Data can be displayed by the display 66 in real time as the data is being collected, or it can be stored in the memory 64 and displayed at a later time. In some embodiments, the display 66 and/or memory 64 may be omitted.

Figure 2:
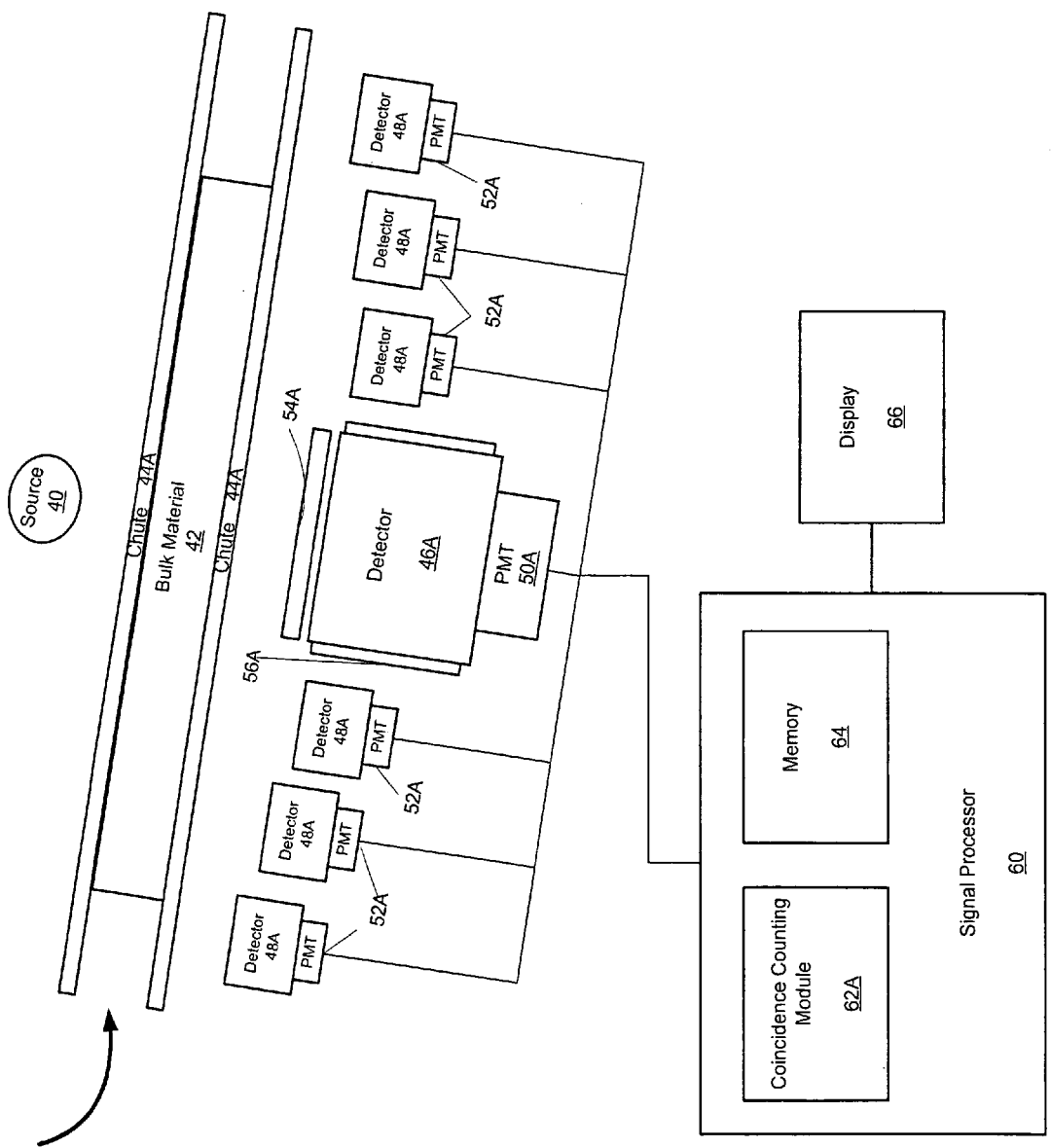
FIG. 2 is a schematic diagram of a gamma ray detector assembly having a detector array and a chute positioned to provide analysis of a bulk material and a data processor according to embodiments of the present invention.

Various detector configurations and sizes can be used according to embodiments of the present invention. For example, the detector assembly in FIG. 2 illustrates a relatively large detector 48A and a photomultiplier tube 50A and an array of smaller detectors 46B and photomultiplier tubes 52A. As used herein, an "array" refers to two or more detectors. The detector 46A may be surrounded by a shielding material, such as shielding material 56A and shielding sheet 54A, such as a lithium, boron, or gadolinium shielding sheet. The detectors 48A may be surrounded by a similar shielding material (not shown). The coincidence counting module 62A can determine events in coincidence between the detectors 46A, 46B. For example, the coincidence counting module 62A can determine if an event occurs in one of the smaller detectors 48A within a predetermined time of another event in the larger detector 46A. As illustrated in FIG. 2, the bulk material is passed through a chute 44A. Like numbered elements can be similar to the elements described in FIG. 1 and are not further described.

Figure 3:
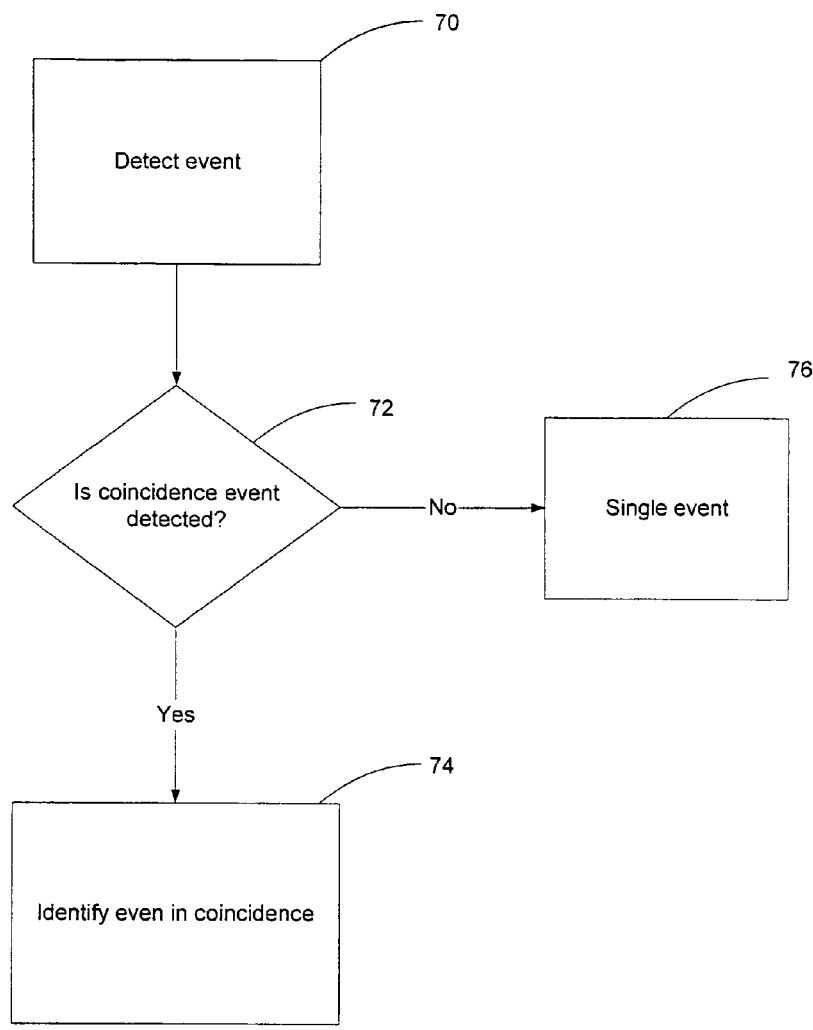
FIG. 3 is a flow chart illustrating operations according to embodiments of the present invention.

Operations according to embodiments of the current invention and that can be carried out by coincidence counting module 62 are shown in FIG. 3. An event is detected (Block 70), for example, by detectors 46, 48 (FIG. 1) or detectors 46A, 48A (FIG. 2). If another event is detected in coincidence with the first event (Block 72), the event or events can be identified as a coincidence event (Block 74). The coincidence events can be further analyzed and/or isolated in a dataset. If a coincidence event is not detected (Block 72), then the event is a single event (Block 76). Single events can be stored in memory (memory 64 in FIGS. 1 and 2) and/or displayed. Alternatively, single events may be discarded from the dataset.

Various coincidence counting techniques and/or parameters for counting coincidence events may be used. Examples of coincidence counting parameters include the total coincidence, coincidence between any event and an event within a prescribed energy, and coincidence between events that sum to a predetermined energy. However, any subset of events in one detector can be selected and events that are in coincidence with the selected subset can be identified. The total coincidence between two detectors includes all events in one detector that are in coincidence with the other detector. Coincidence summing to a predetermined energy include events in one detector that are in coincidence with events in another detector only if the energy of the two events sum to a predetermined energy level. Typical energy ranges are between and about 0.5 to about 11 MeV for the configuration shown in FIGS. 1 and 2. For example, gamma ray energies from carbon and oxygen are 4.44 MeV and 6.13 MeV respectively. Depending on detector resolution, these peaks may be detected in various energy ranges. For example, the carbon 4.44 MeV peak is typically detected in a range between 4.2 to about 4.6 MeV for a NaI detector and between about 4.35 and 4.45 in a Ge detector due to increased resolution in a Ge detector. The 6.13 MeV oxygen peak is typically detected in a range between about 5.9 MeV to about 6.3 MeV in a NaI detector and between about 6.05 MeV and about 6.2 MeV in a Ge detector. As another example, sulfur can include gamma ray energies of 5.420 MeV and 3.221 MeV. Other exemplary energy levels of sulfur are listed in Table 2.

Embodiments of the present invention will now be described with respect to the following non-limiting examples.

EXAMPLE 1

Hydrogen Peak Reduction

When activated by thermal neutrons, hydrogen de-excites by emitting a single prompt gamma ray with energy 2.223 MeV. The magnitude of this peak in a non-coincidence spectrum is often one or more orders of magnitude larger than other elements of interest. Thus, hydrogen can dominate the energy range below and including 2.223 MeV. This is due to the Compton continuum of that gamma ray. This poses a difficulty in analyzing the spectrum at and below 2.223 MeV.

Because the hydrogen gamma ray is a single gamma ray, coincidence counting can substantially eliminate it and its continuum from the spectrum. In this example, two HPGe detectors having 59% and 72% efficiency, respectively, were placed at a 180 degrees angle with respect to each other such as in the configuration illustrated in FIG. 1. A thermal neutron beam produced by the PULSTAR educational reactor at North Carolina State University (NCSU) was used as the source 40. The PULSTAR reactor is a 1 MW pool-type research reactor with 4% enriched, pin-type fuel consisting of uranium dioxide pellets in zircaloy cladding. The distance between the two detectors was approximately 23 cm and the sample was placed in between them at an angle of 45 degrees. A silicon sample was used and placed in the thermal neutron beam of the NCSU PULSTAR reactor.

Figure 4:
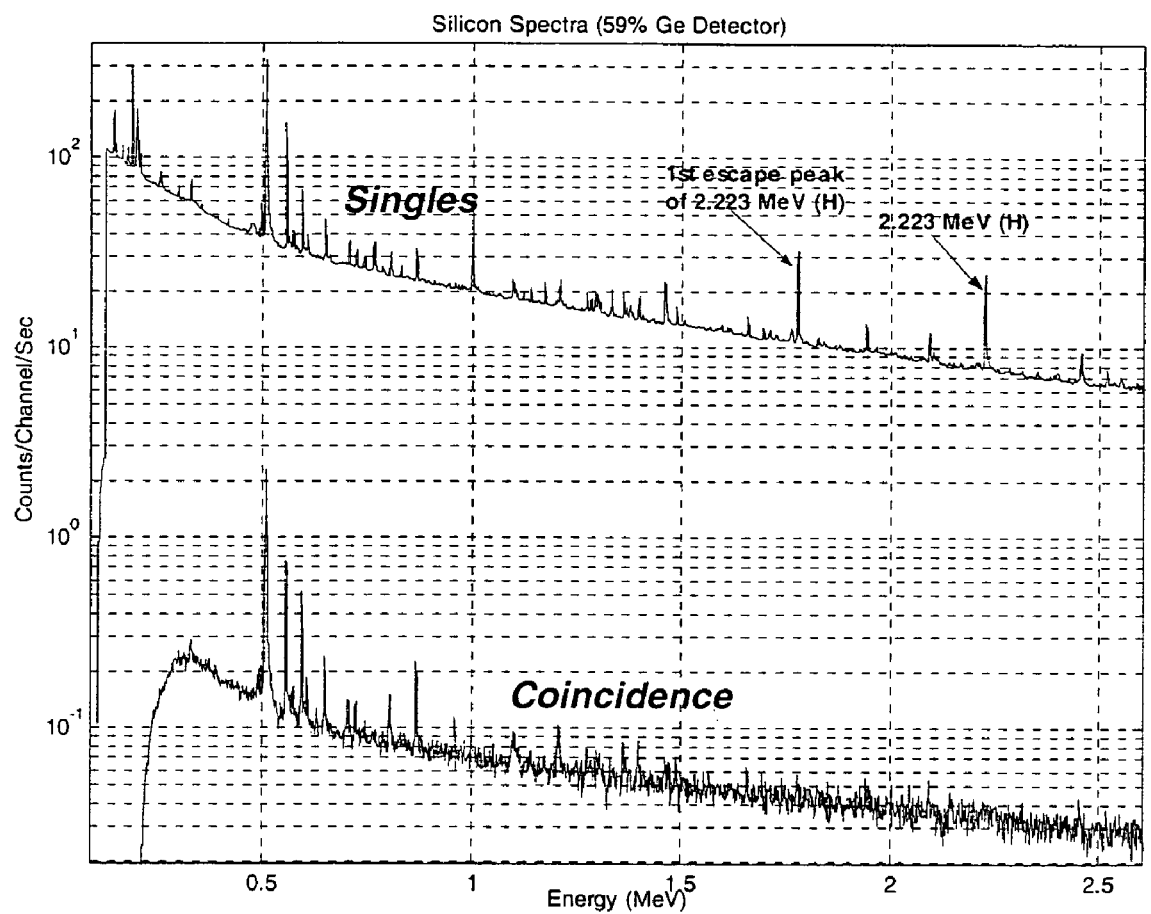
FIG. 4 is a graph illustrating the reduction or elimination of a hydrogen peak in a silicon sample according to embodiments of the present invention.

FIG. 4 shows the singles and coincidence spectra of the silicon sample from the 59% HPGe detector. The energy range 0–2.5 MeV is shown. It can be seen from the coincidence spectrum that the hydrogen peak (and thus its continuum) is substantially eliminated.

EXAMPLE 2

Background and Sum Peak Reduction

Figure 5:
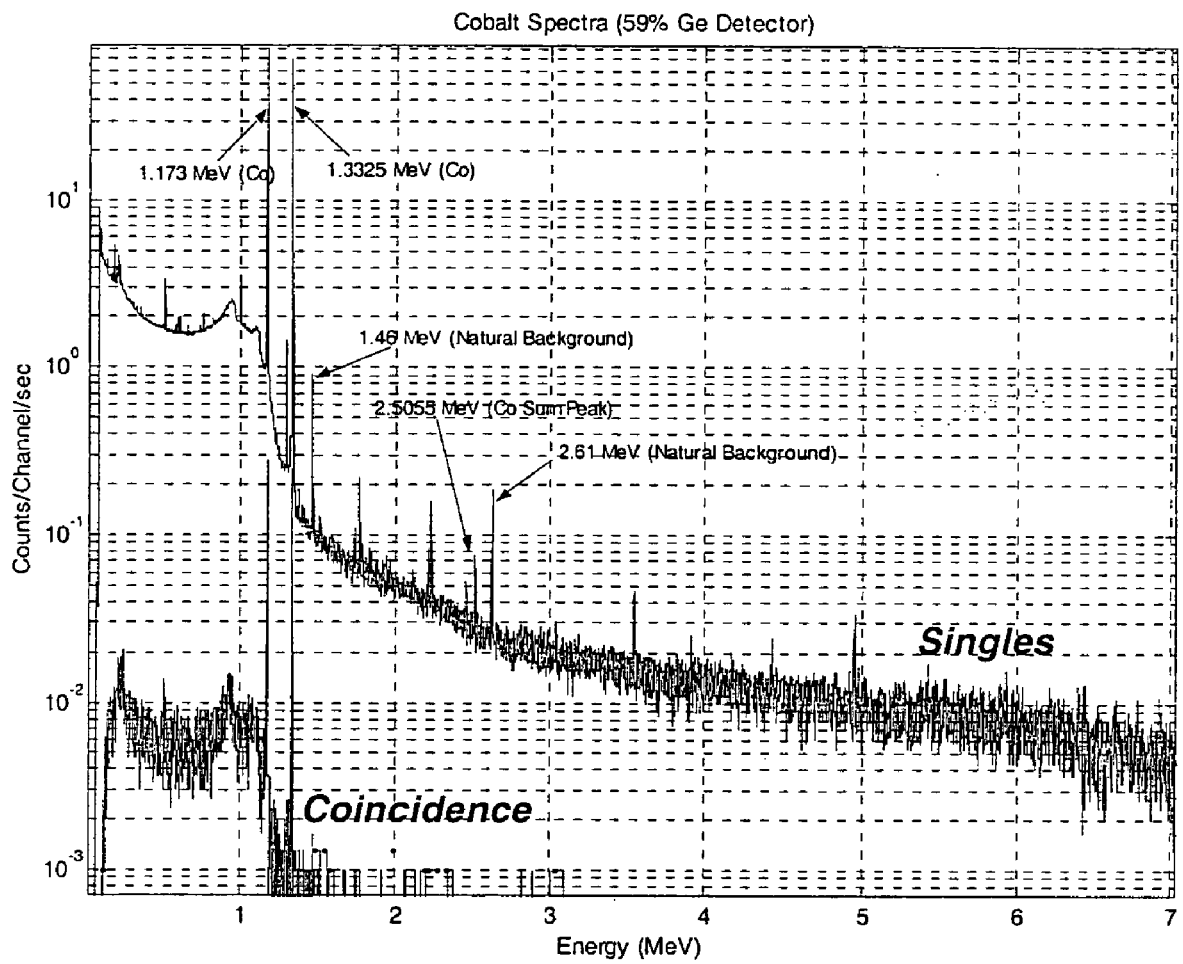
FIG. 5 is a graph illustrating the reduction or elimination of background and summation peak(s) for a cobalt-60 radioisotope sample according to embodiments of the present invention.

A cobalt-60 radioisotope to simulate "bulk material" was used for this experiment with two HPGe detectors (59% and 72% efficiency) in the configuration shown in FIG. 1. Because cobalt-60 is a radioisotope, a neutron source was not required or used in this example. The experiment was conducted in the NCSU PULSTAR reactor bay while the reactor was in operation. The resulting spectra are shown in FIG. 5. Because the reactor was operating at the time of the experiment, there was a high background level in the singles spectrum. Observing the coincidence spectrum, the 2.505 MeV cobalt summation peak was substantially eliminated. The background from long-lived natural radioisotopes (1.462 MeV, 2.614 MeV, and surrounding structural material) is also made negligible.

EXAMPLE 3

Pulse Pile Up Reduction

Figure 6:
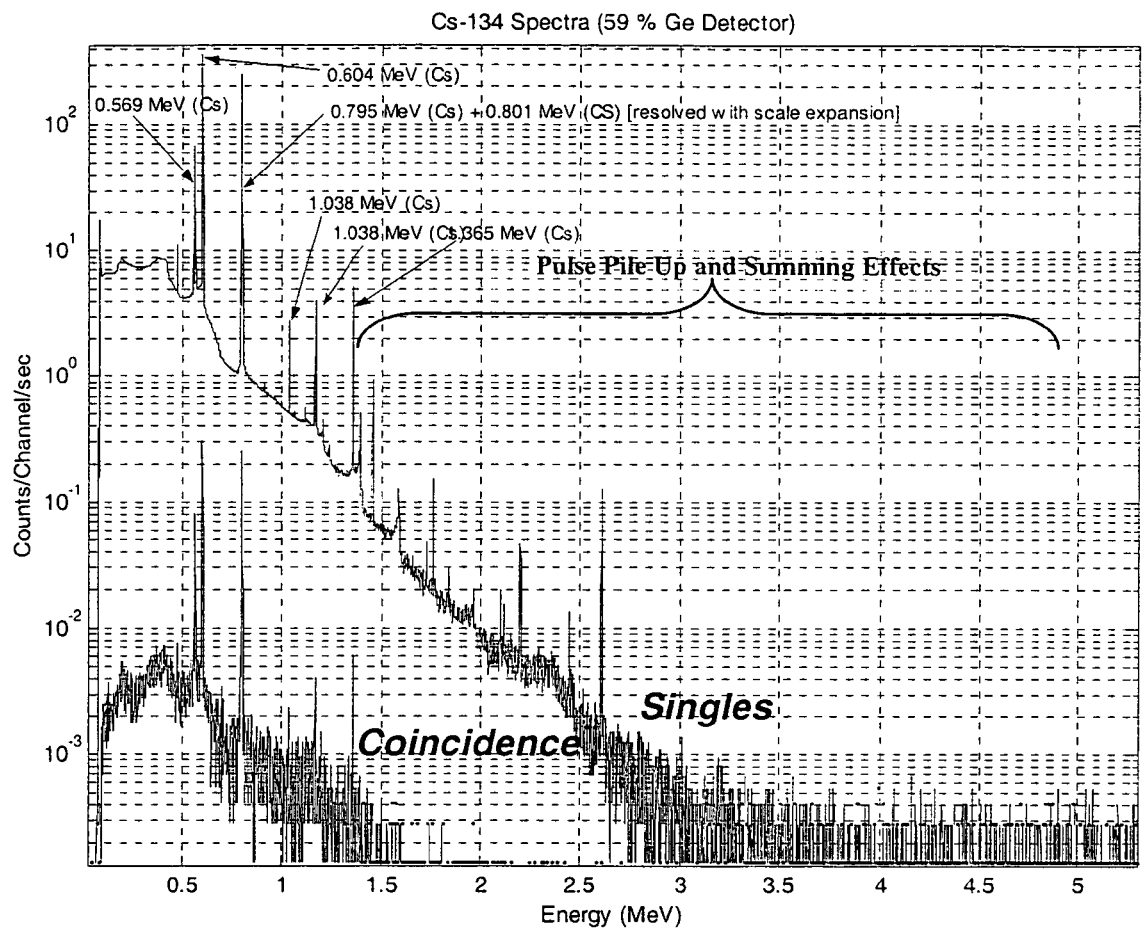
FIG. 6 is a graph illustrating reduction or elimination of the pulse pile up effects for a cesium-134 radioisotope sample according to embodiments of the present invention.

A cesium-134 radioisotope to simulate "bulk material" was used for this experiment with two HPGe detectors (59% and 72% efficiency) in the configuration shown in FIG. 1. Because cesium-134 is a radioisotope, a neutron source was not required or used in this example. The highest energy gamma ray for Cs-134 is 1.365 MeV. The experiment was conducted in a lab where the background radiation level was low. Thus, any peaks or continuum above the 1.365 MeV may be due to summing and pulse pile up effects respectively as seen in FIG. 6. In the coincidence spectrum above 1.365 MeV, visible peaks and a negligible continuum can be observed. It may be noted that this observation is a function of the counting rate. As the counting rate increases, the pulse pile up effects become more observable in the single event and coincidence spectra obtained.

EXAMPLE 4

Two-Dimensional Spectra

Two examples of two-dimensional spectra obtained via the multiparameter data acquisition capability are presented. "Two-dimensional spectra" refers to spectra obtained in an array when a detector pair is used for coincidence measurements. If more than two detectors are used, the number of obtained arrays may correspond to the different number of detector combinations. In general, two-dimensional spectra can provide more information than the one dimensional spectra and may be used, as an example, for decay scheme analysis.

The two-dimensional spectra can be presented on three-dimensional plots where each of the X and Y axis represent a detector in the detector pair used. The Z axis represents the obtained event counts. The plots thus take the form of a three dimensional surface where the peaks represent intense coincidence areas.

To illustrate the two-dimensional spectra, two Germanium (Ge) detectors were used having 72% efficiency and 59% efficiency. The detectors were set in a horizontal position with a 90 degrees angle with respect to each other. The sample was placed at the intersection of the centerlines on both detectors, 15 cm away.

Figure 7:
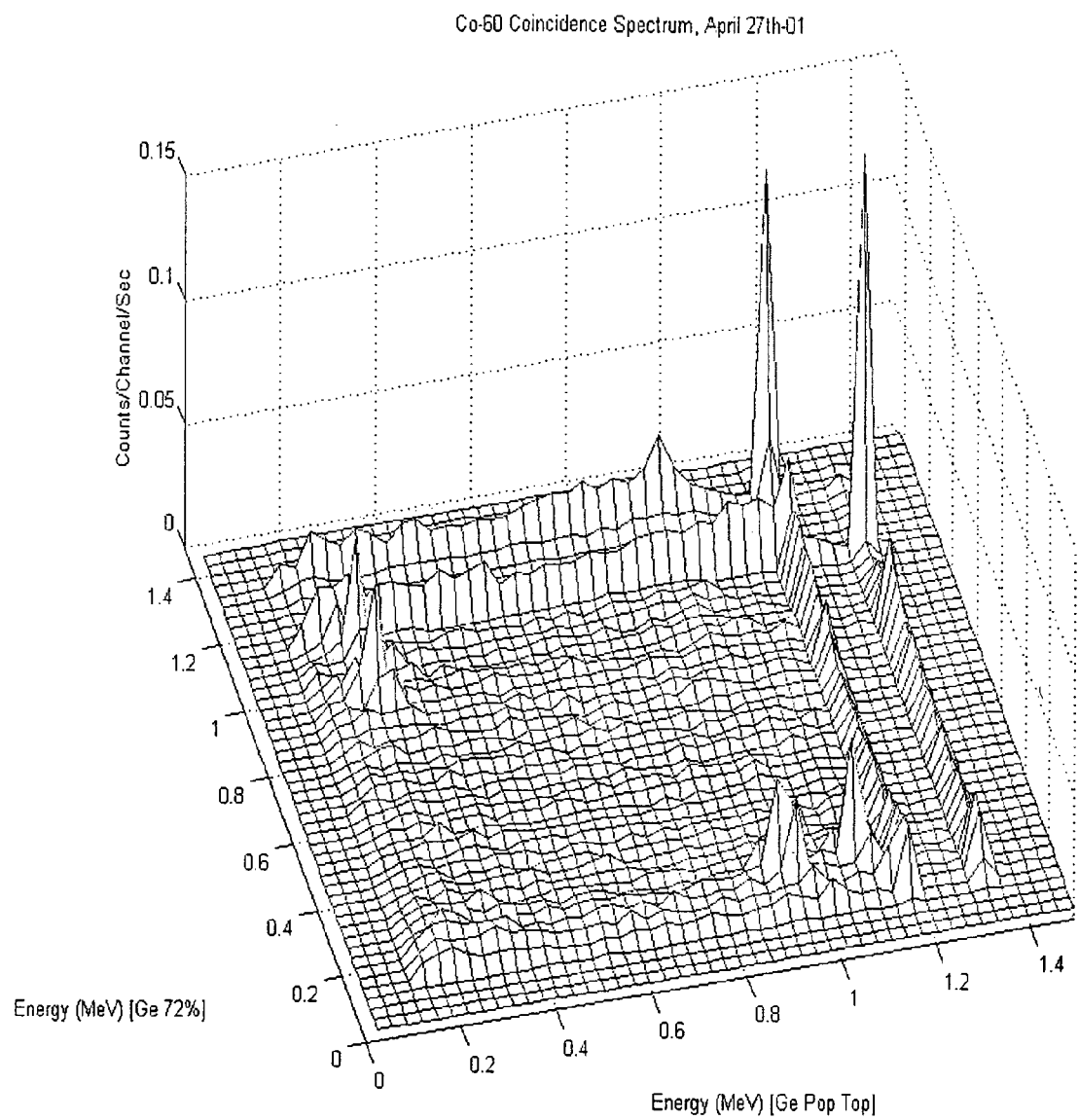
FIG. 7 is graph illustrating a two-dimensional spectrum for a cobalt-60 radioisotope sample according to embodiments of the present invention.
Figure 8:
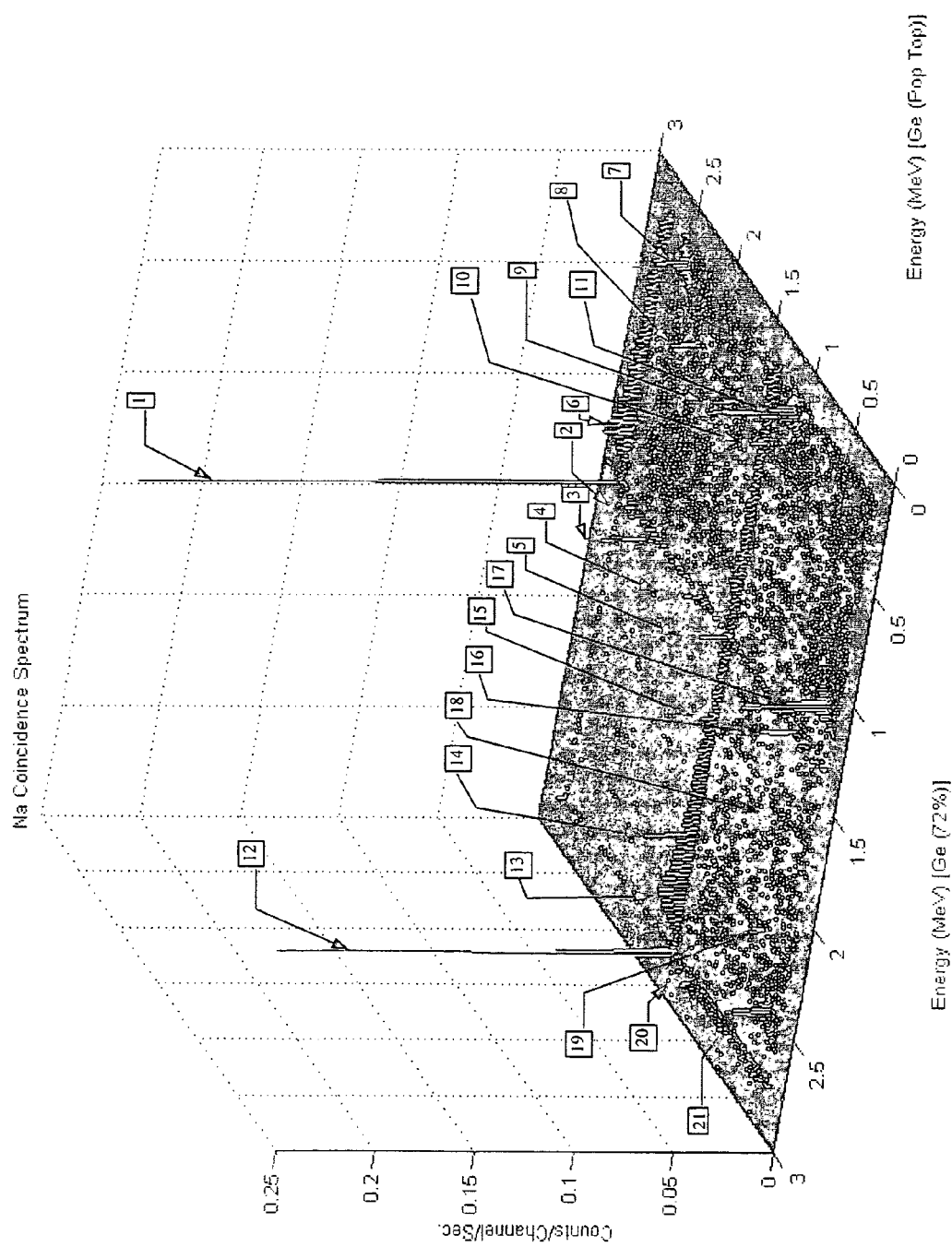
FIG. 8 is a graph illustrating a two-dimensional spectrum for a sodium coincidence spectrum according to embodiments of the present invention.

Two examples are presented. The first example, FIG. 7, shows the two-dimensional spectrum of cobalt-60. Certain features of this spectrum are noted in FIG. 7, such as the pulse pile up and summing effects in the single count spectrum. The second example, FIG. 8, is for Na-24, which is a more complicated spectrum than Co-60. Certain of the features of FIG. 8 are explained in Table 1. The detectors were placed at 90 degrees with respect to each other, and, therefore the 135° edge appears in FIGS. 7 and 8 instead of the normal Compton edge.

2. Projecting a horizontal (or vertical) range of the spectrum to one of the axes. This is called horizontal (or vertical) window summing. On one of the axes, this would represent an energy range equivalent to the width of the window. On the other axis, this would represent the spectrum that is in coincidence with this energy range.
3. Projecting a diagonal area of the spectrum to one of the axes.
4. Projecting an irregular range of the spectrum to one of the axes. This type of projection depends on the type of physical problem being considered. Examples of this are not presented herein.

Projecting a diagonal area in the two-dimensional spectrum to one of the axes has a different interpretation. For gamma-gamma coincidence measurements, the spectrum obtained from this projection yields the gamma spectrum in one detector that corresponds to a specific total energy deposition in both detectors. The total energy deposited may be equal to the Q-value (total energy) of the reaction studied or the sum of two individual gamma-ray energies, or other values of interest.

TABLE 1

Na-24 Two-dimensional Spectrum Features

| # | Pop Top Ge Detector | 72% Ge Detector |
|---|---|---|
| | Peaks Correspond to in the | |
| [1] | 2.754 MeV Na-24 γ | 1.368 MeV Na-24 γ |
| [2] | 135° edge of the 2.754 MeV Na-24 γ | 1.368 MeV Na-24 γ |
| [3] | $1^{st}$ escape of the 2.754 MeV Na-24 γ | 1.368 MeV Na-24 γ |
| [4] | $2^{nd}$ escape of the 2.754 MeV Na-24 γ | 1.368 MeV Na-24 γ |
| [5] | 1.368 MeV Na-24 γ | 1.368 MeV Na-24 γ |
| | Chance Coincidence | |
| [6] | 2.754 MeV Na-24 γ | 135° edge of the 1.368 MeV Na-24 γ |
| [7] | 135° edge of the 2.754 MeV Na-24 γ | Backscatter γ the 2.754 MeV Na-24 γ |
| [8] | $1^{st}$ escape of the 2.754 MeV Na-24 γ | 0.511 MeV Annihilation γ |
| [9] | $2^{nd}$ escape of the 2.754 MeV Na-24 γ | 0.511 MeV Annihilation γ |
| [10] | 1.368 MeV Na-24 γ | 0.511 MeV Annihilation γ |
| [11] | 135° edge of the 1.368 MeV Na-24 γ | Backscatter γ the 1.368 MeV Na-24 γ |
| [12] | 1.368 MeV Na-24 γ | 2.754 MeV Na-24 γ |
| [13] | 1.368 MeV Na-24 γ | 135° edge of the 2.754 MeV Na-24 γ |
| [14] | 1.368 MeV Na-24 γ | $1^{st}$ escape of the 2.754 MeV Na-24 γ |
| [15] | 1.368 MeV Na-24 γ | $2^{nd}$ escape of the 2.754 MeV Na-24 γ |
| [16] | 0.511 MeV Annihilation γ | 1.368 MeV Na-24 γ |
| [17] | Backscatter γ the 1.368 MeV Na-24 γ | 135° edge of the 1.368 MeV Na-24 γ |
| [18] | 0.511 MeV Annihilation γ | $2^{nd}$ escape of the 2.754 MeV Na-24 γ |
| [19] | 0.511 MeV Annihilation γ | $1^{st}$ escape of the 2.754 MeV Na-24 γ |
| [20] | 135° edge of the 1.368 MeV Na-24 γ | 2.754 MeV Na-24 γ |
| [21] | 135° edge of the 2.754 MeV Na-24 γ | Backscatter γ the 2.754 MeV Na-24 γ |

EXAMPLE 5

Two-Dimensional Diagonal Summing

Two-dimensional spectra are presented in a flat view where the intense coincident areas are now defined by the darker areas in the plot. Extracting part (or all) of the information from the flat view plots can transform them into normal two-dimensional plots. This is normally done by summing (e.g., projecting) a certain area in the two-dimensional plot along one of the axes. This projection can be made in the following ways:

1. Projecting the whole spectrum area to one of the axes. This can provide the total coincidence spectrum in one of the detectors. This is the same as summing all the rows (or columns) in the coincidence data array.

Figure 9:
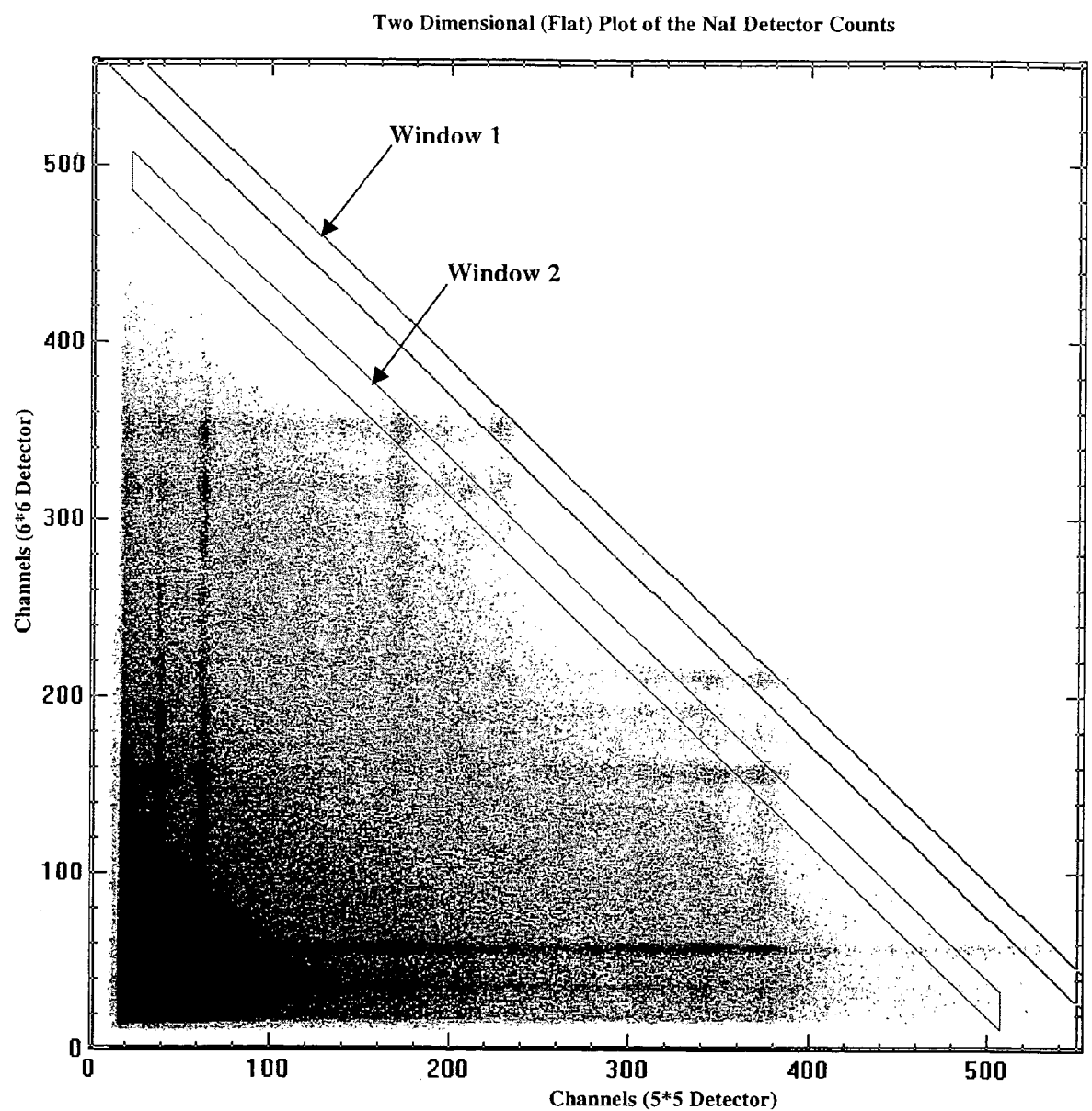
FIG. 9 is a graph illustrating a two-dimensional (flat view) of the events in two NaI detectors using a sulfur sample according to embodiments of the present invention.

The diagonal area is generally defined by two diagonal lines labeled Window 1 and Window 2 in FIG. 9. The slope of the chosen diagonal lines depends on the calibrations of the two detectors. Two factors generally can be used to determine the window width. The first factor is the energy of interest. The energy can either be a single energy or a range of energies. A common energy of interest is the Q-value, or total energy, of the reaction studied. If one of the decay schemes of the element of interest has only two gamma rays, these two gammas may be shown when making the diagonal projection.

The second factor that can play a role in determining the window width is the detector resolution. If the two detectors used have the same resolution, regardless of the detector type, a window may be used that has a constant width along the diagonal. The reason for this constant window width is that, for diagonal summing, the low energy in one detector corresponds to a high energy in the other detector and vice versa. This width may be determined by the detector resolution at the highest energy of interest. If the detectors have different resolutions, the window can have a trapezoidal shape. The wide base of the trapezoidal shape can correspond to the highest energy in the detector with the poorest resolution.

EXAMPLE 6

Coincidence Scheme Application

Two examples are presented for using the two-dimensional diagonal summing for coincidence scheme identification application. The first example is for sulfur. The two detectors used were NaI with dimensions 5"×5" and 6"×6". The experimental setup was similar to that shown in FIG. 1. The resolution for these detectors is almost the same, thus a constant width window was used for the diagonal summing. FIG. 9 shows the two-dimensional plot (flat view) of the counts in both NaI detectors. Two windows are outlined and labeled Window 1 and Window 2. Window 1 corresponds to the Q-value of the $^{32}S(n,\gamma)^{33}S$ reaction, and Window 2 corresponds to an energy of 7.800 MeV. The significance of the 7.800 MeV energy will be discussed.

Figure 10:
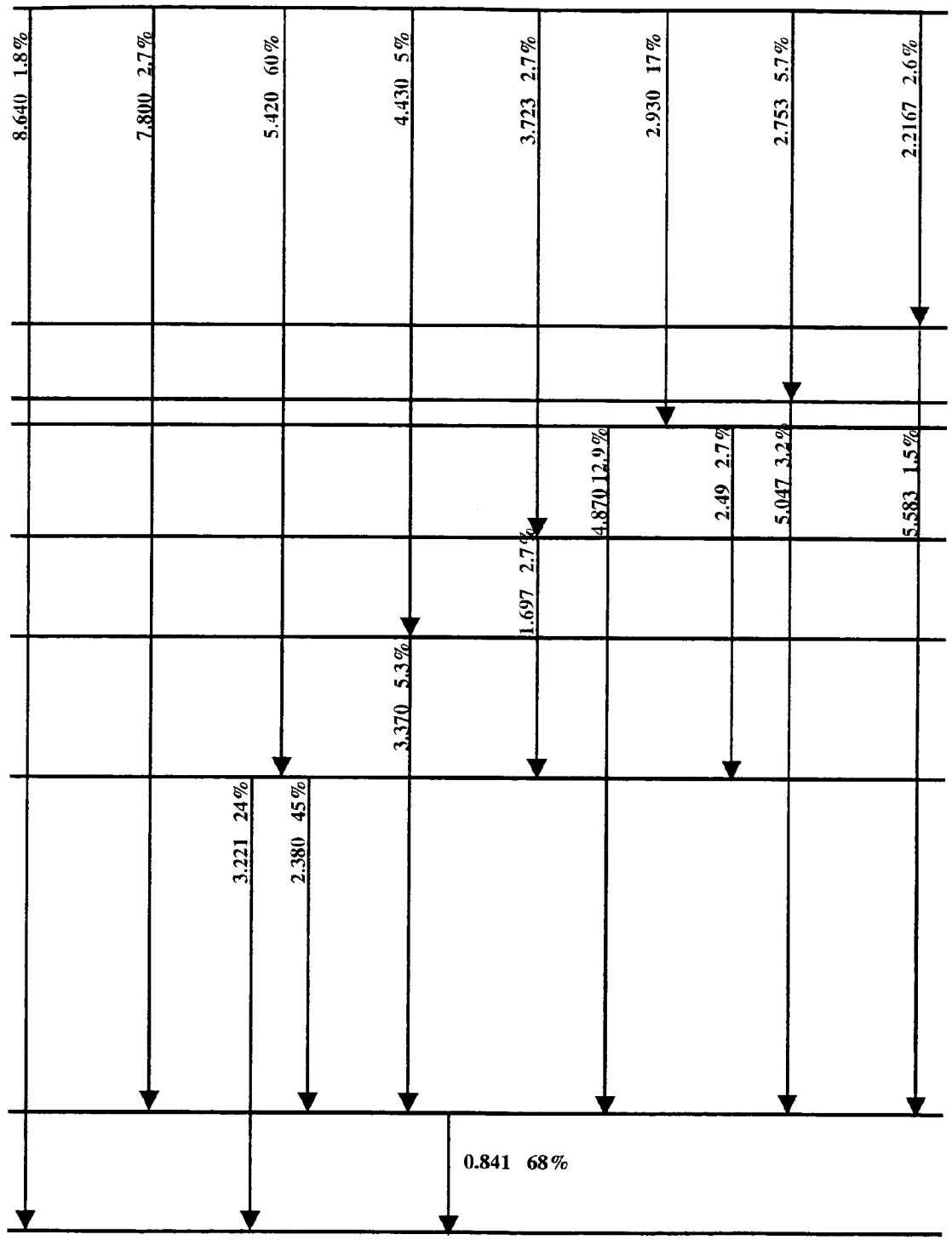
FIG. 10 is a chart illustrating the sulfur-33 gamma ray decay levels and a Q-value of 8.64165 MeV according to embodiments of the present invention.

The level scheme that is used to analyze this data is shown in FIG. 10 (see Raman S., R. F. Carlton, and Wells J. C., "Thermal neutron Capture Gamma Rays from Sulfur Isotopes: Experimental and Theory", Physical Review C, 31(1) (1985), pp. 18–69), along with the gamma intensities and energies (in MeV). This scheme shows 17 gamma rays out of a total of 103 for $^{33}S$. The scheme probabilities deduced from this decay scheme are shown in Table 2, where it is shown that approximately 93% of the transitions in the $^{33}S$ decay scheme may be accounted for.

TABLE 2

Scheme Probabilities for $^{33}S$

| Scheme | Energies in Scheme (MeV) | Scheme Probability (%) |
| --- | --- | --- |
| 1 | 8.640 | 1.8 |
| 2 | 7.800–0.841 | 3.0 |
| 3 | 5.420–3.221 | 21 |
| 4 | 5.420–2.380–0.841 | 39 |
| 5 | 4.430–3.370–0.841 | 5.0 |
| 6 | 3.723–1.697–3.221 | 1.5 |
| 7 | 3.723–1.697–2.380–0.841 | 1.5 |
| 8 | 2.930–4.870–0.841 | 13 |
| 9 | 2.930–2.49–3.221 | 1.5 |
| 10 | 2.930–2.49–2.380–0.841 | 1.5 |
| 11 | 2.753–5.047–0.841 | 3 |
| 12 | 2.216–5.583–0.841 | 1.5 |
| | Total | 93.3% |

Figure 11:
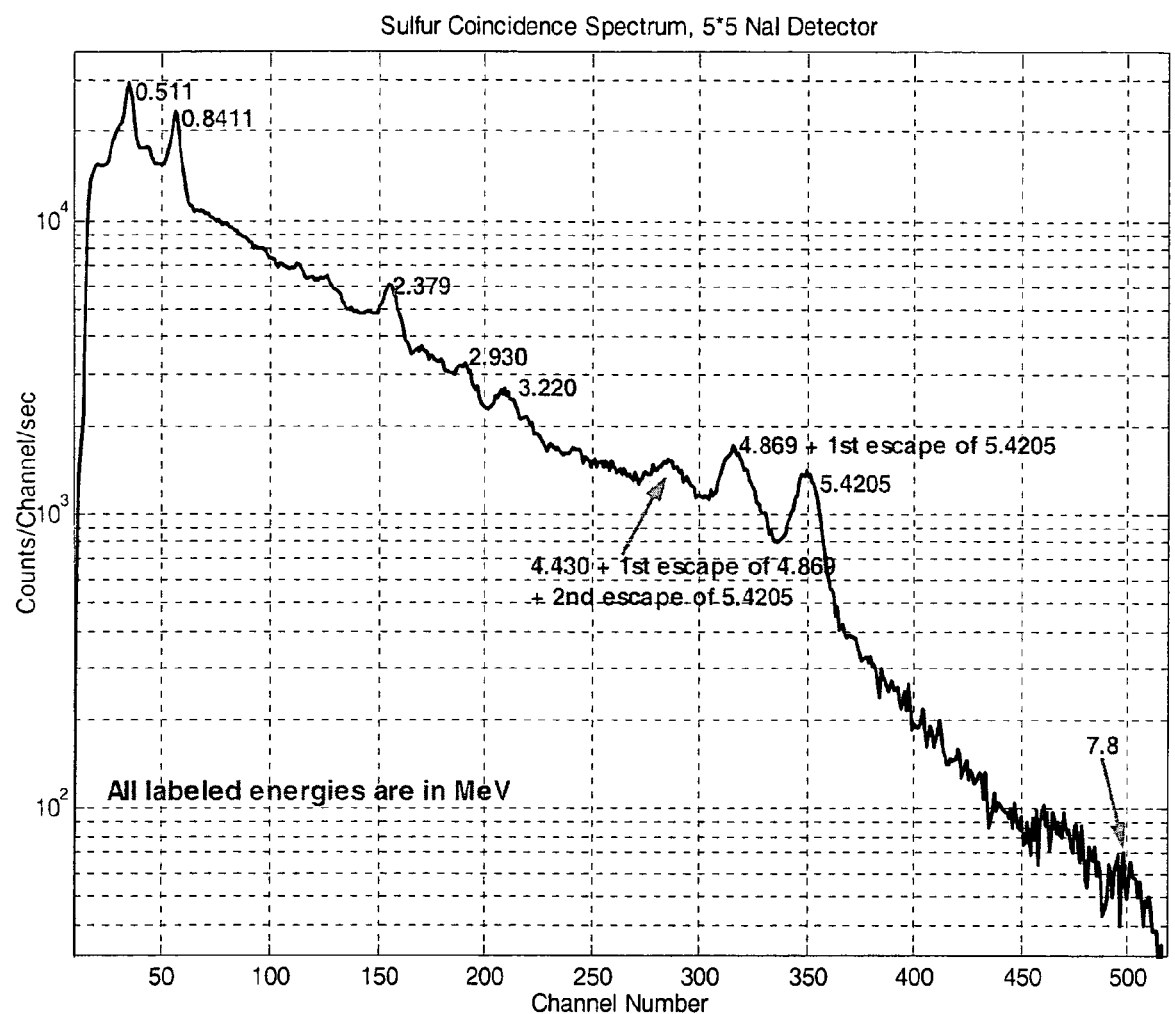
FIG. 11 is a graph illustrating a two-dimensional full spectrum projection for a sulfur sample according to embodiments of the present invention.

The total coincidence spectrum in one of the detectors is shown in FIG. 11. This can be obtained by performing the first type of projection (summing) stated earlier. FIG. 11 shows the result of projecting the whole spectrum to the x-axis, i.e. the total coincidence spectrum in the 5"×5" NaI detector in coincidence with all events in the 6"×6" NaI detector.

Figure 12:
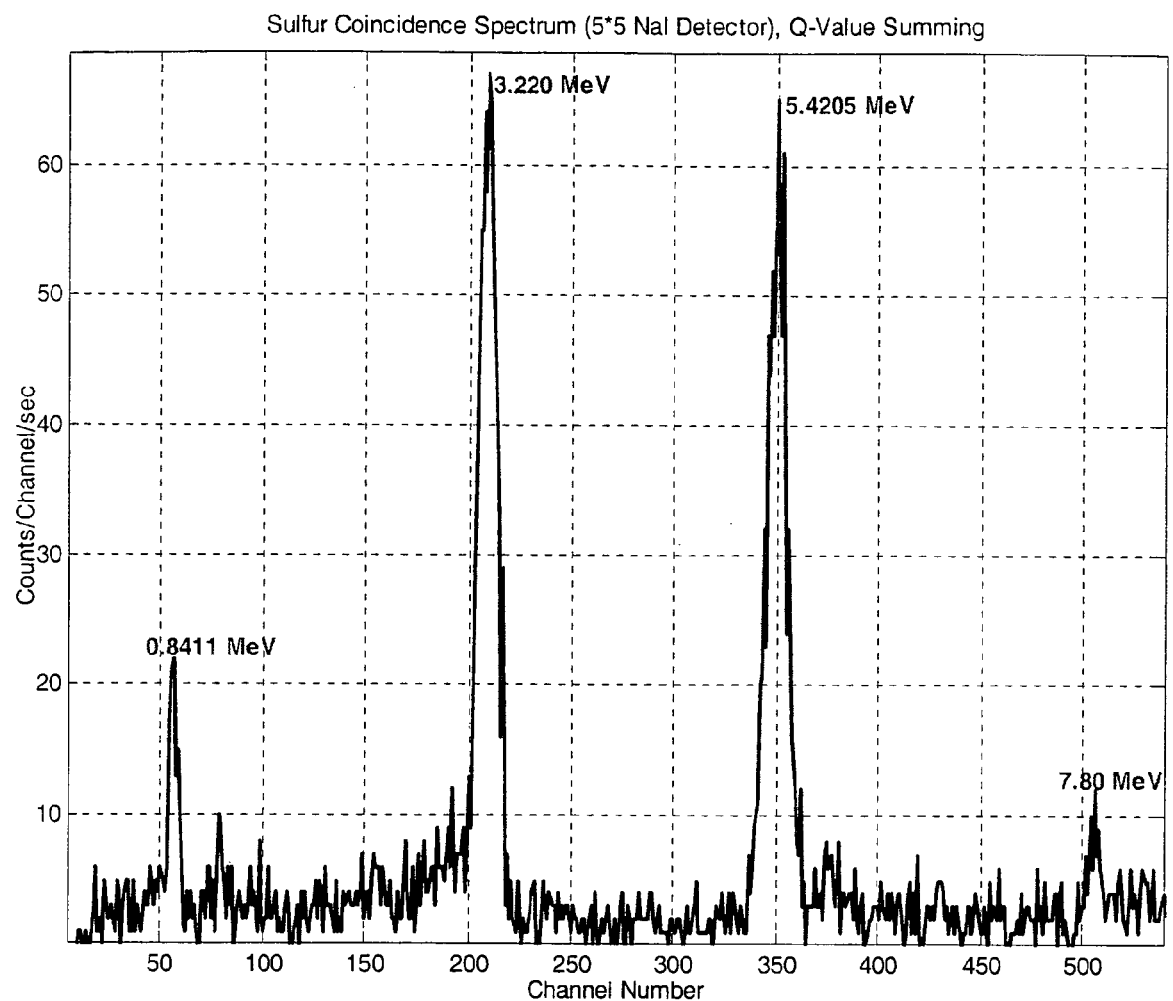
FIG. 12 is a graph illustrating a spectrum obtained using Q-value diagonal summing techniques for a sulfur sample according to embodiments of the present invention.

Next, the resulting spectrum is analyzed by performing a diagonal summation. FIG. 12 shows the projection of Window 1 in FIG. 9. The energy of Window 1 corresponds to the Q-value of the $^{32}S(n,\gamma)^{33}S$, 8.64 MeV. As seen in Table 2, the second and third schemes are the only schemes that contain two gamma rays in them. The energies of the second scheme are 7.800 and 0.841 MeV while those for the third scheme are 5.420 and 3.221 MeV. Thus, it is expected that these four gamma rays may be observed when performing Q-value diagonal summation. See FIG. 12. It also shows that the 5.420–3.221 MeV pair are much more intense than the 7.800–0.841 MeV pair. This can be attributed to the difference in scheme probability.

An early paper, Hoogenboom, A. M., "A New Method in Gamma-Ray Spectroscopy: A Two Crystal Scintillation Spectrometer with Improved Resolution", Nuclear Instruments, 3 (1958), pp. 57–68, demonstrated a hardware approach to obtain spectra that result from a specific sum of gamma ray energies. This approach was proposed to greatly improve the peak resolutions over those obtained from a normal singles spectrum. The diagonal summing approach used here can provide the same type of spectrum but with much more accuracy and flexibility. Moreover, to examine another Q-value or sum, one can simply interrogate the same data with the different diagonal sum by use of a single set of data from the current electronic system (and KmaxNT).

Figure 13:
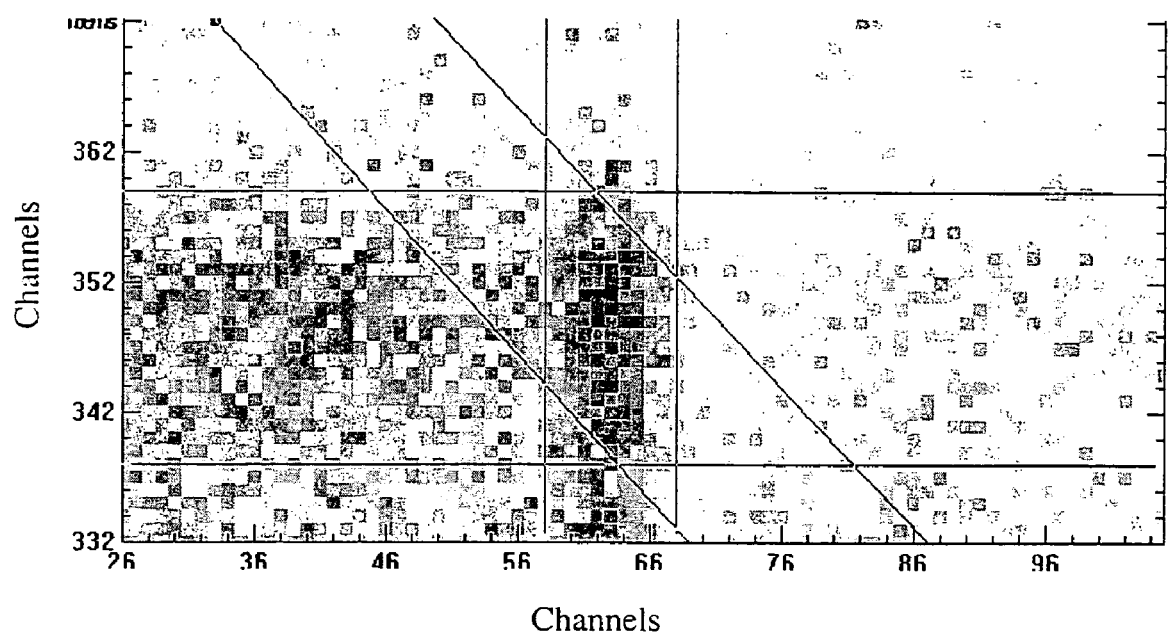
FIG. 13 is an expanded view of the graph of FIG. 9 illustrating resolution improvements that can be obtained using diagonal summing techniques according to embodiments of the present invention.

In addition to the improved peak resolution obtained from diagonal summation over the singles spectrum, there may also be a noticeable improvement over the total coincidence spectrum. This improvement may be enhanced as the energy increases. To illustrate this, FIG. 13 shows an expanded view of the two-dimensional (flat) sulfur spectrum. The intense area corresponds to the 0.8411 MeV gamma ray in one detector and the 5.4205 MeV gamma ray in the other detector. Projecting in the vertical direction yields the 0.8411 MeV peak while projecting in the horizontal direction yields the 5.4305 MeV peak in the other detector. If the projections were performed on the area confined between the diagonal lines, peaks corresponding to the same energies can be obtained with improved resolution, i.e., a narrower peak. The improved resolution may be due to the multiplication of the two Gaussian shaped peaks that constitute the new peak. Another useful effect is the substantial minimization of the relatively flat parts of the spectra that underlie the peaks that are a result of Compton scattering, i.e., "background". This effect can greatly improve the statistics within the peaks because the peaks are no longer positioned on large, relatively flat continua in the spectra that contributes to increased statistical fluctuations in the peak areas. It also can be seen from FIG. 13 that higher energies are affected more than the lower energies.

Figure 14:
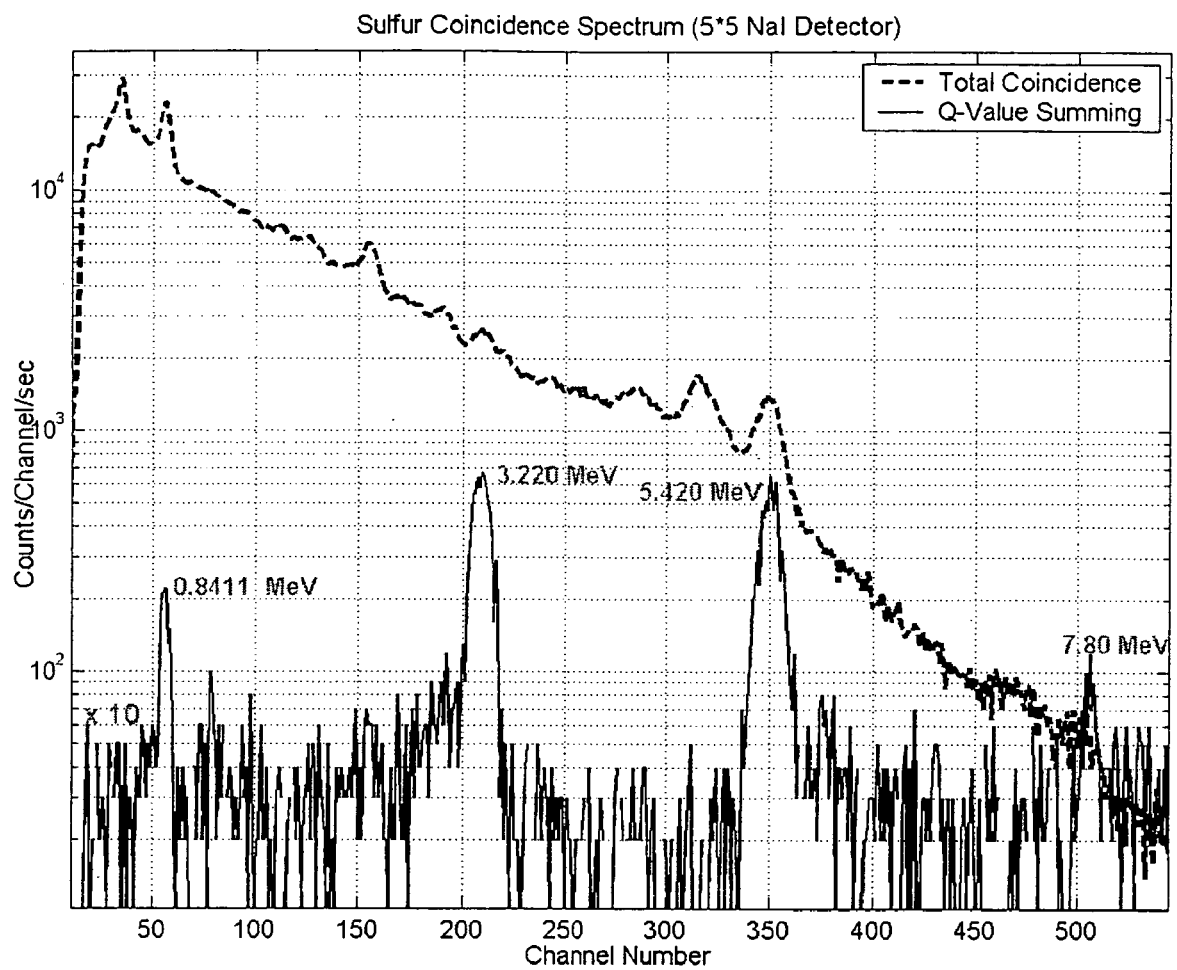
FIG. 14 is a graph illustrating a comparison between spectra obtained using the total coincidence and Q-value diagonal summing for a sulfur sample according to embodiments of the present invention.

FIG. 14 shows the Q-value diagonal summing spectrum compared with the total coincidence spectrum. The peak resolution improvement may be shown.

Figure 15:
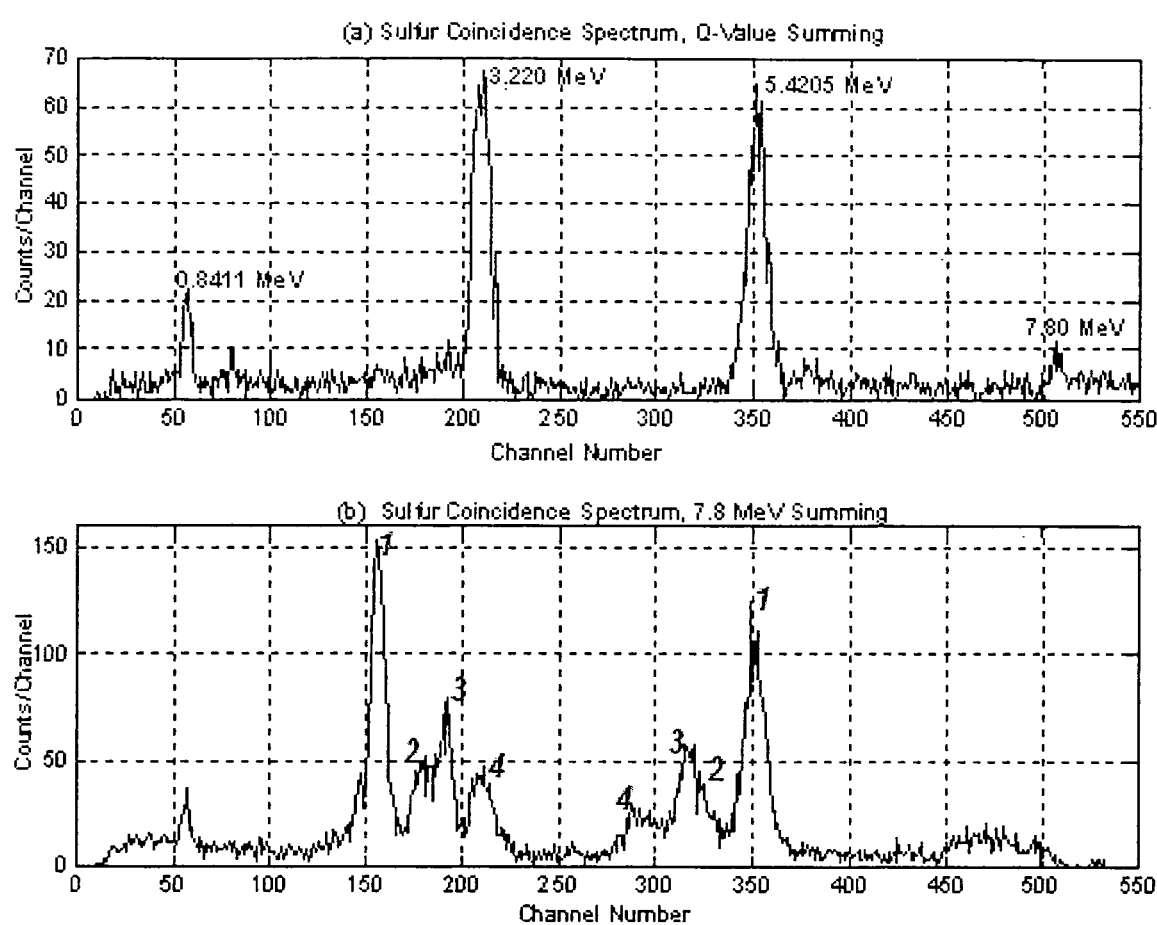
FIG. 15 is a graph illustrating the spectra obtained using diagonal summing techniques using the Q-value and an energy level of 7.8 MeV for a sulfur sample according to embodiments of the present invention.

FIG. 15 shows diagonal summing spectra for the Q-value and 7.8 MeV. Observing the decay scheme of $^{33}S$, FIG. 10, one finds several energies that add up to 7.8 MeV. These energies are labeled on FIG. 15 as pair numbers 1 through 4. The energies corresponding to these pairs are listed in Table 3.

TABLE 3

Energies Adding Up To 7.8 MeV in the $^{33}S$ Decay Scheme

| Pair # | Energies in Coincidence (MeV) |
| --- | --- |
| 1 | 5.4205 and 2.379 |
| 2 | 5.047 and 2.753 |
| 3 | 4.870 and 2.931 |
| 4 | 5.4205 Compton and 3.22 |

The second example presented for diagonal summing is for mercury. The NCSU PULSTAR thermal neutron beam was utilized in this experiment. The two NaI detectors (5"×5" and 6"×6") were positioned facing each other with the sample in between. The sample-to-detector distance was 20 cm. The sample was natural mercury (12 gm).

Table 4 shows the naturally abundant isotopes in Mercury and their characteristics. The factor in Table 4 corresponds to the product of the abundance and the (n,γ) cross section of each isotope. Using this factor, it can be shown that approximately 95% of the (n,γ) interactions will occur with $^{199}$Hg isotope. The $^{199}$Hg(n,γ)$^{200}$Hg has a Q-value of 8.028 MeV. This can be selected as the energy used for the diagonal summing.

Figure 16:
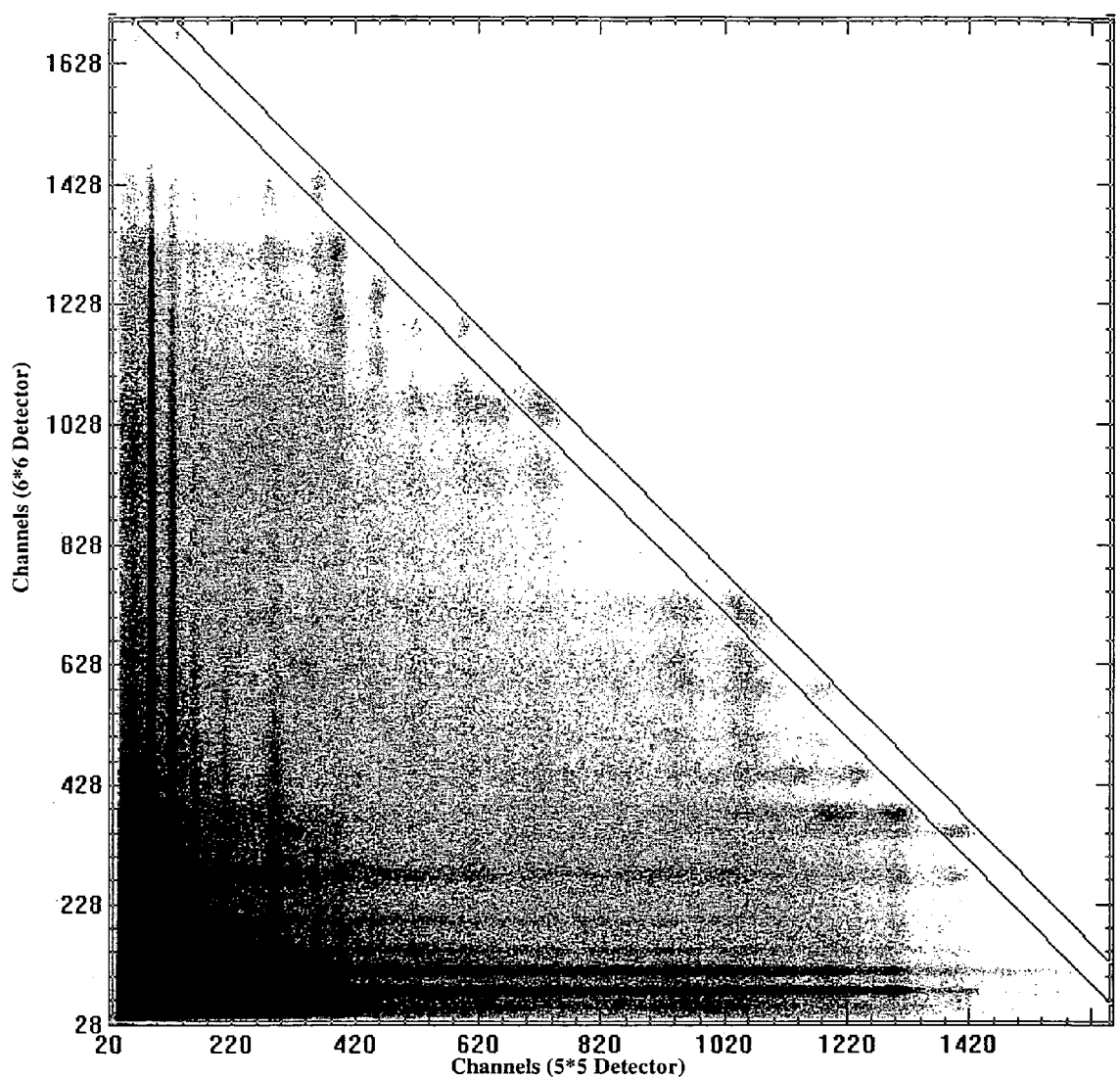
FIG. 16 is a two-dimensional (flat view) graph of the events in two NaI detectors for a mercury sample according to embodiments of the present invention.

FIG. 16 shows the two-dimensional plot (flat view) of the counts in both NaI detectors. The outlined diagonal window corresponds to the Q-value of the reaction.

TABLE 4

Isotopes in Natural Mercury and their characteristics

| Isotope | Abundance, % | $\sigma_\gamma$ (b) | Factor* | Normalized Factor |
|---|---|---|---|---|
| Hg-196 | 0.15 | 3100 | 465 | 1.18% |
| Hg-198 | 10 | 1.9 | 19 | 4.83E−2% |
| Hg-199 | 16.9 | 2200 | 37180 | 94.55% |
| Hg-200 | 23.1 | 60 | 1386 | 3.5% |
| Hg-201 | 13.2 | 8 | 105.6 | 0.268% |
| Hg-202 | 29.8 | 4.9 | 146.02 | 0.371% |
| Hg-204 | 6.85 | 0.4 | 2.74 | 6.97E−3% |

*Factor = Abundance × σ

Figure 17:
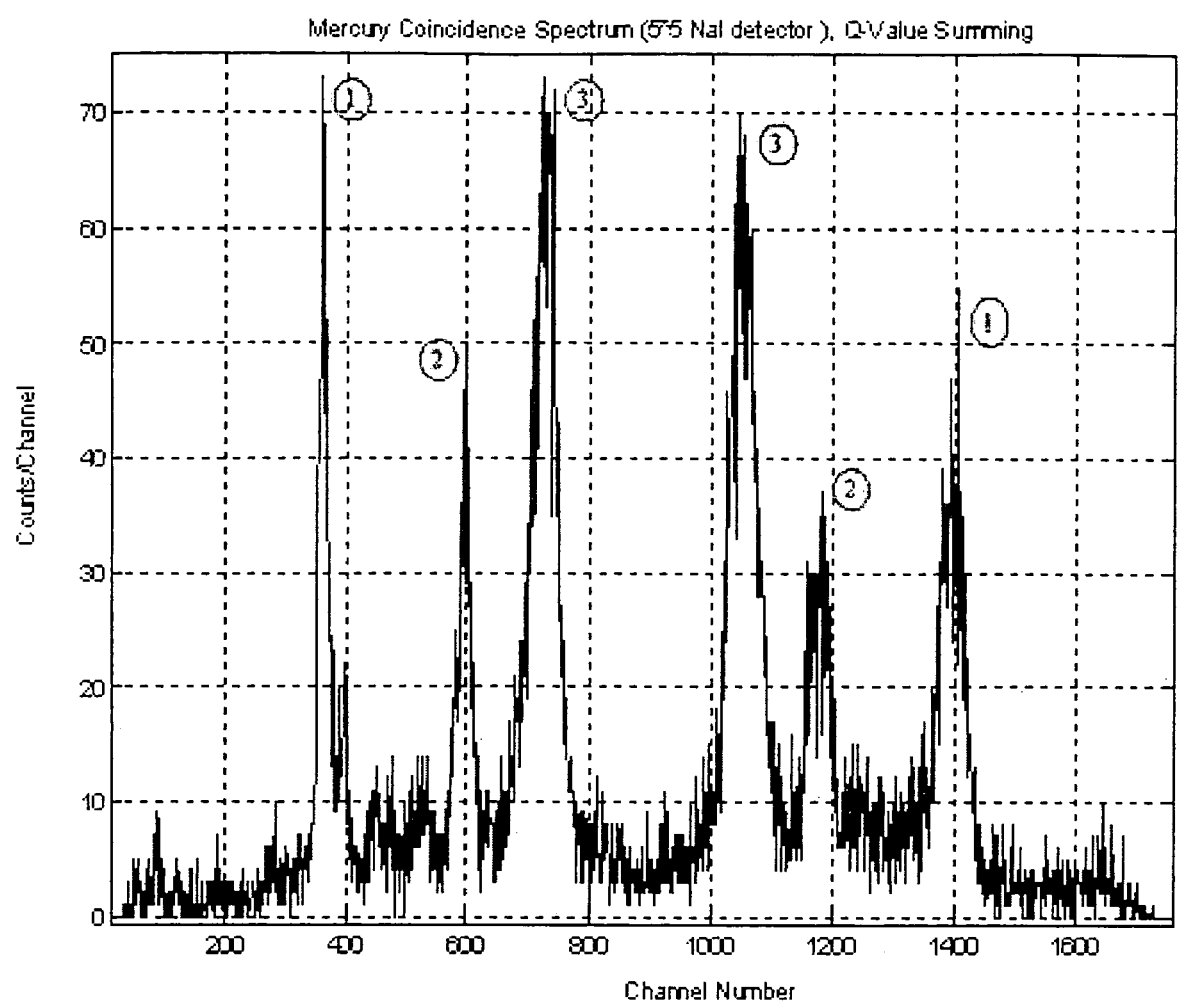
FIG. 17 is a graph illustrating a spectrum obtained using Q-value summing techniques for a mercury sample according to embodiments of the present invention.

FIG. 17 shows the Q-value diagonal summing for natural Mercury. The dominant coincidence pairs are labeled in FIG. 17 and their corresponding energies are listed in Table 5.

TABLE 5

Energies Adding Up To 8.02 MeV in the $^{200}$Hg Decay Scheme

| Pair # | Energies in Coincidence (MeV) |
|---|---|
| 1 | 1.571 and 6.457 |
| 2 | 2.639 and 5.387 |
| 3 | 3.288 and 4.739; 3.185 and 4.841 |

Figure 18:
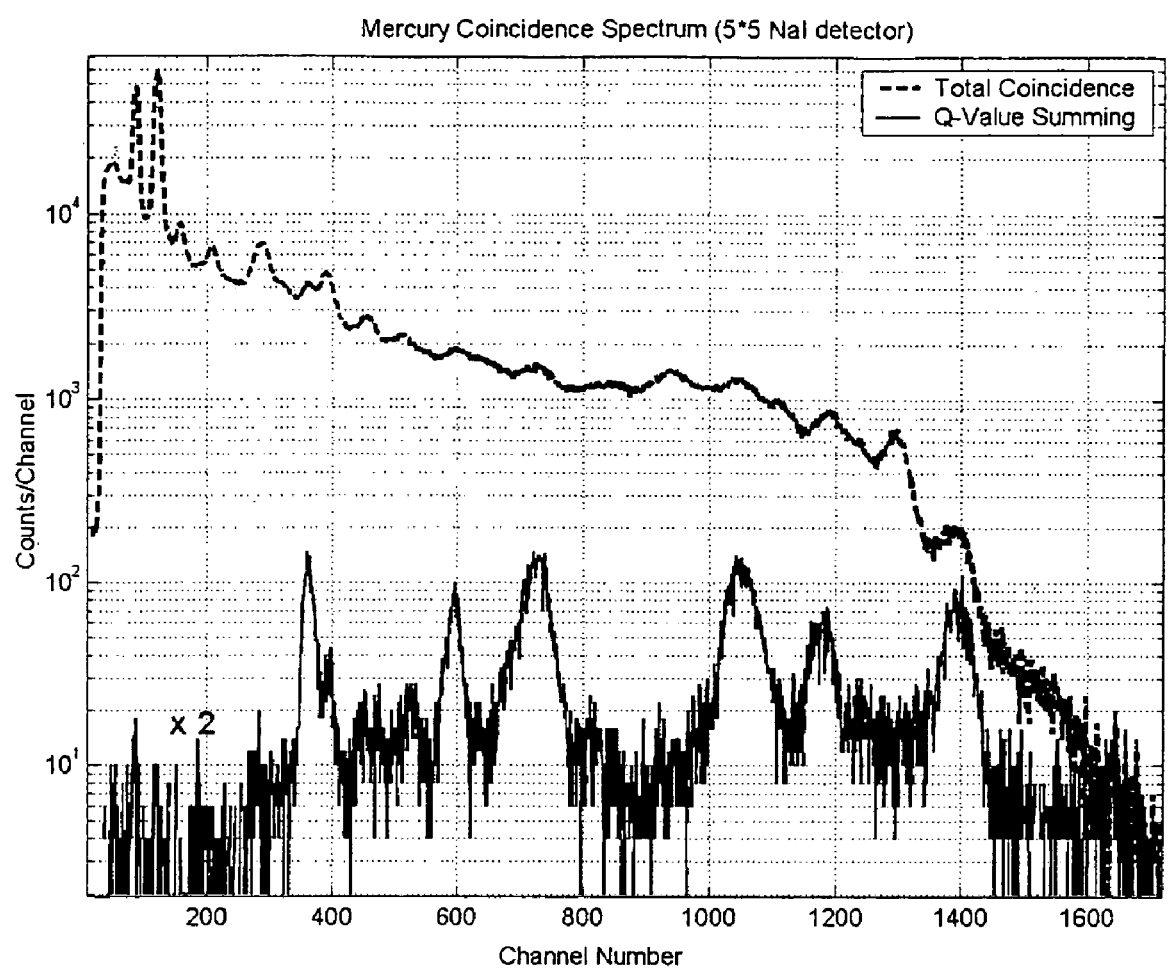
FIG. 18 is a graph illustrating a comparison of the full coincidence spectrum and the Q-value diagonal sum spectrum for a mercury sample according to embodiments of the present invention.

A comparison between the Q-value diagonal summing spectrum and the total coincidence spectrum is shown in FIG. 18. Peak resolution improvement may be shown.

EXAMPLE 7

Elemental Analysis Application

Another application where two-dimensional diagonal summing can be used is elemental analysis. To illustrate this, an experimental arrangement similar to that shown in FIG. 1 was used. The sample used was coal, approximately 22 kg, with 100 grams of mercury (powder form) mixed in it. The techniques in this example can be used to identify the mercury in the sample.

Figure 19:
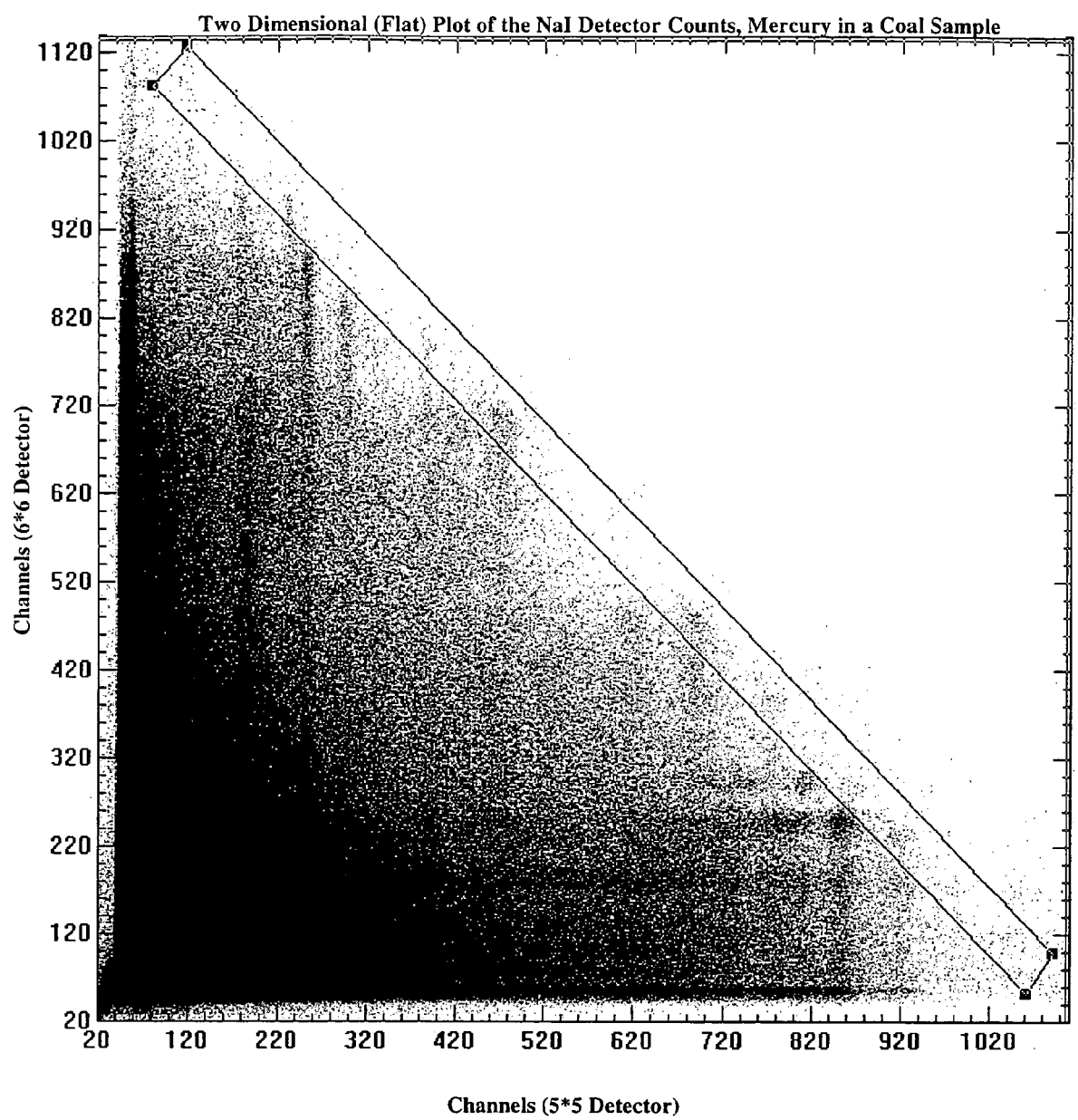
FIG. 19 is a two-dimensional (flat view) graph of the events in two NaI detectors for a coal sample according to embodiments of the present invention.

FIG. 19 shows the two-dimensional plot (flat view) of the counts in both NaI detectors. The outlined diagonal window corresponds to the Q-value of the $^{199}$Hg(n,γ)$^{200}$Hg reaction, 8.028 MeV.

Figure 20:
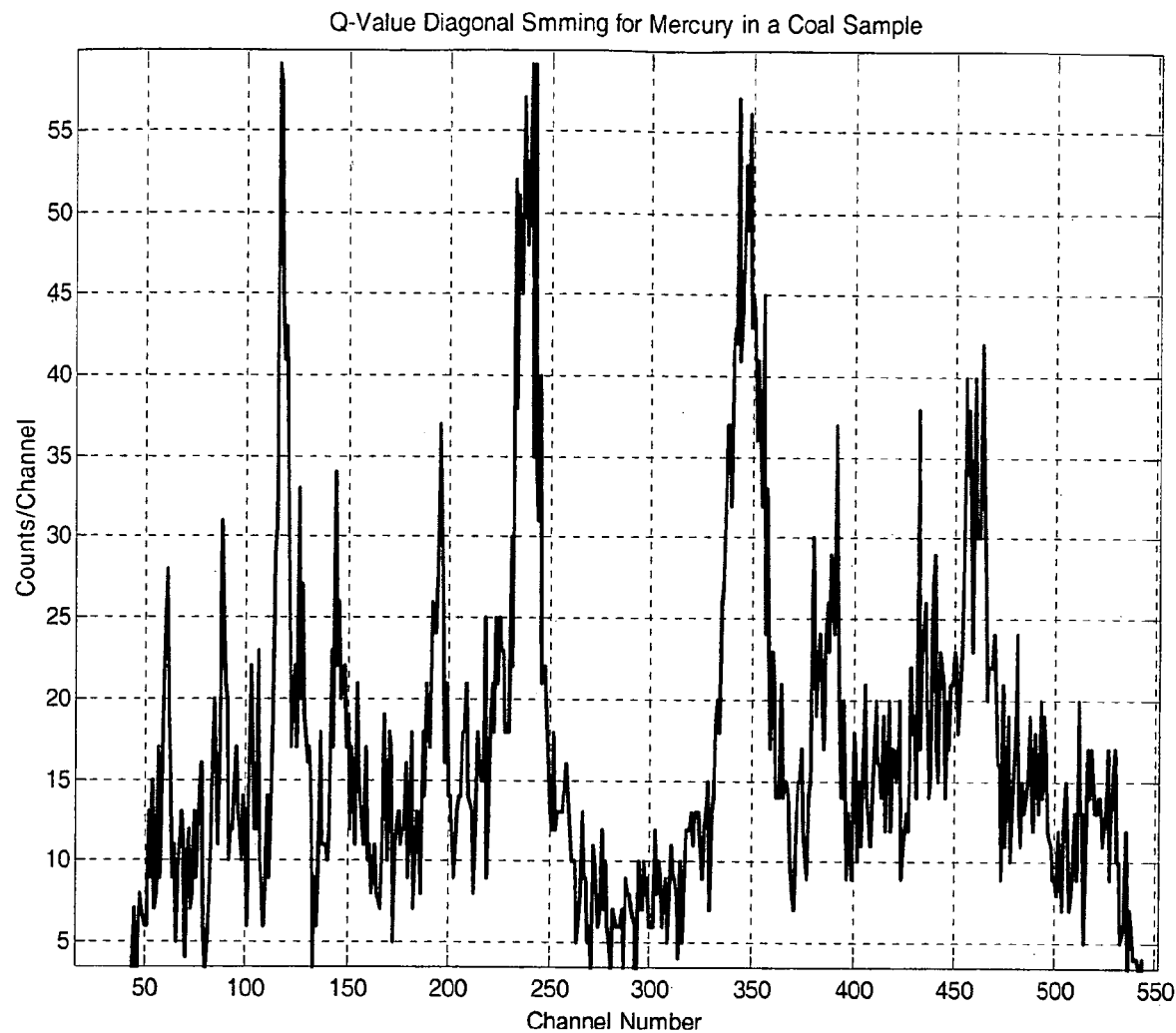
FIG. 20 is a graph illustrating a Q-value diagonal sum spectrum for mercury in a coal sample according to embodiments of the present invention.

FIG. 20 shows the Q-value diagonal summing for outlined window in FIG. 19. There is a resemblance between the obtained spectrum in FIG. 20 and FIG. 17, thus illustrating that mercury could be identified in the coal sample.

EXAMPLE 8

Sulfur

Figure 21:
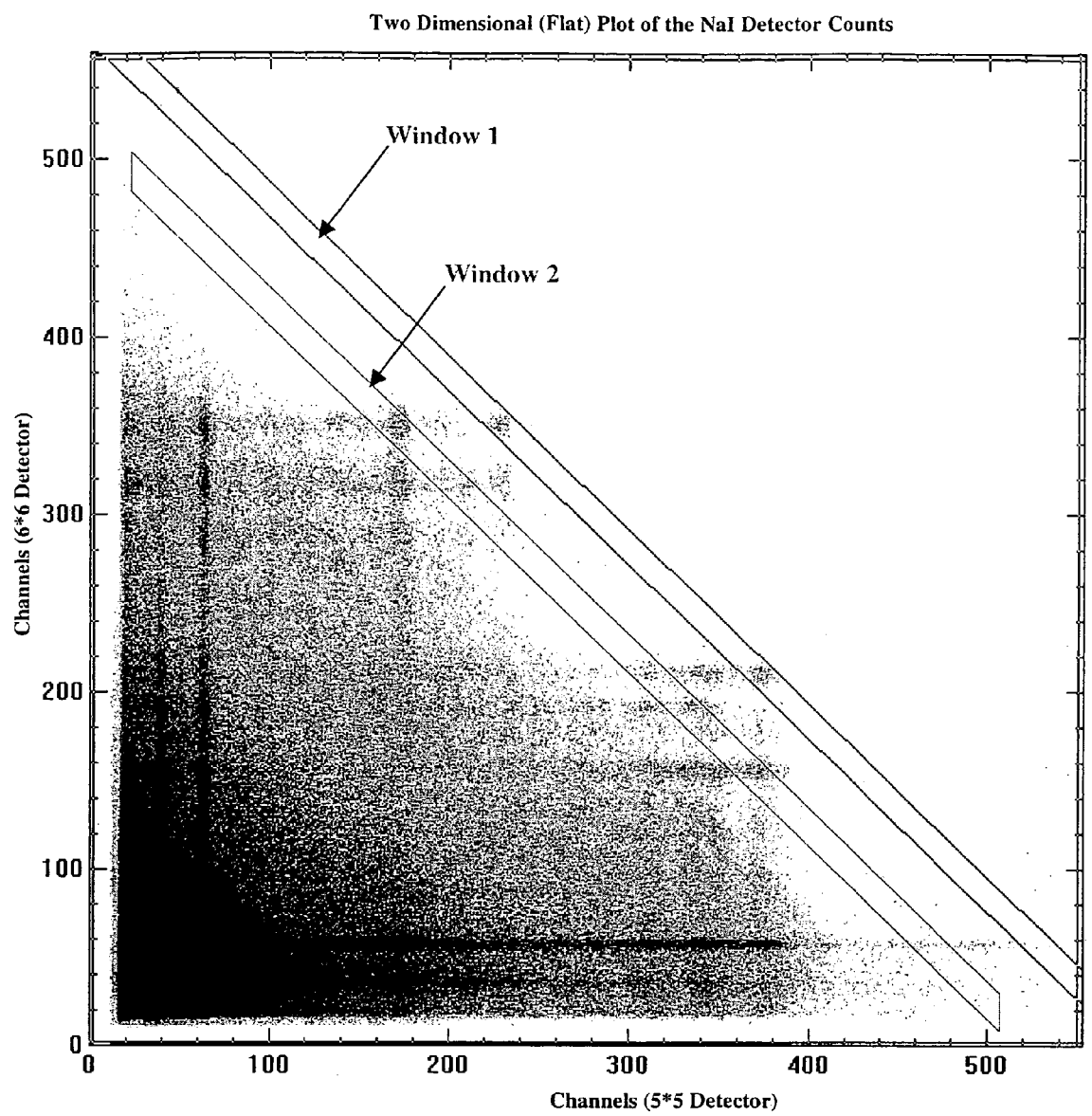
FIG. 21 is a two-dimensional plot (flat view) of the event counts in two NaI detectors for a sulfur sample according to embodiments of the present invention.
Figure 22:
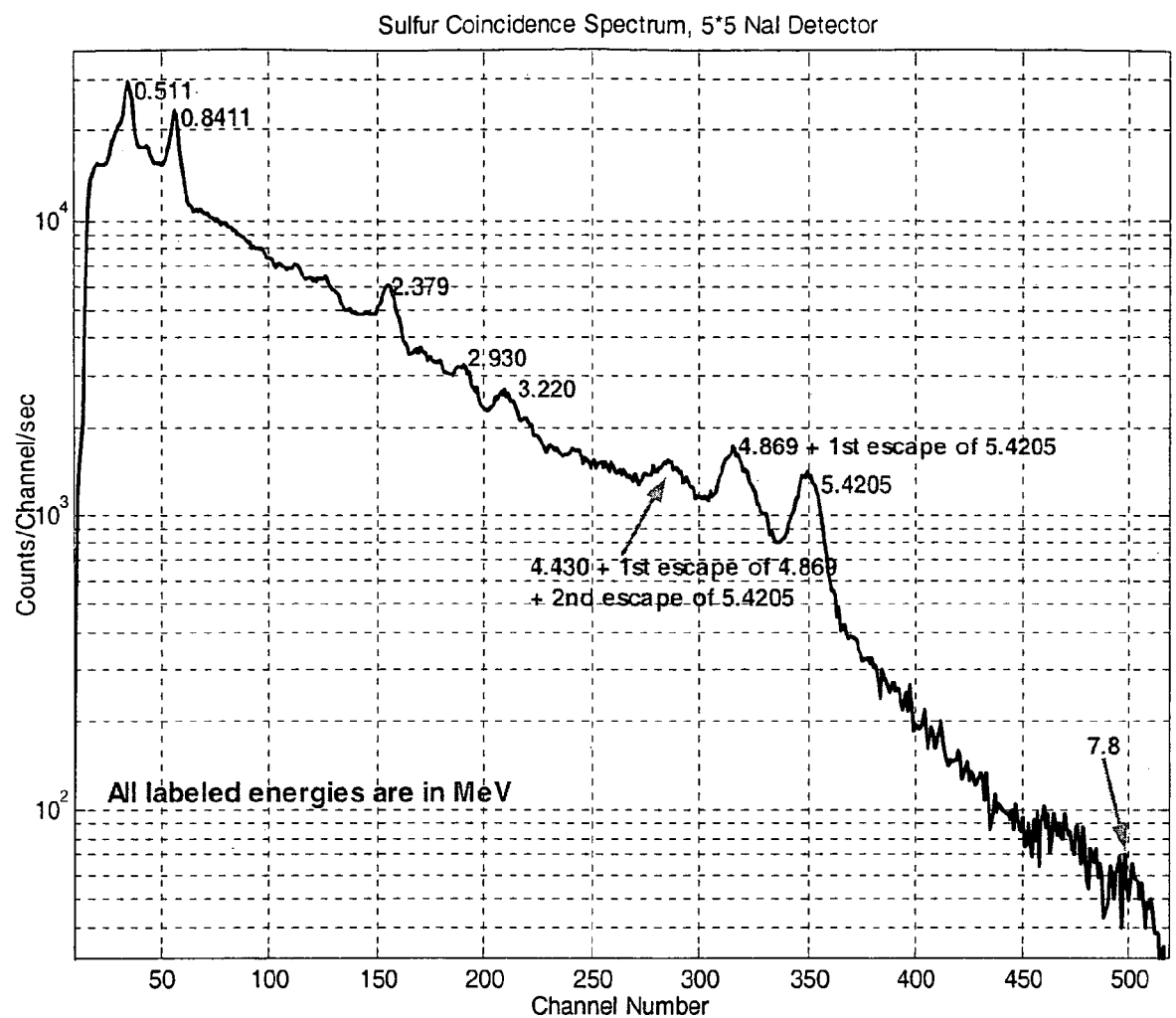
FIG. 22 is a two-dimensional full spectrum projection for the data in FIG. 21 according to embodiments of the present invention.

The two NaI detectors with dimensions 5"×5" and 6"×6" were positioned side-by-side. A box containing sulfur was placed over the detectors, above which a Cf252 neutron source was placed in lead shielding. This configuration is similar to the configuration shown in FIG. 1. The resolution for these detectors was almost the same, and, thus, a constant width window was used for the diagonal summing. The results are shown in FIGS. 21–25. FIG. 21 is a two-dimensional plot (flat view) of the counts in both NaI detectors. Two windows are outlined, Window 1 and Window 2. Window 1 corresponds to the Q-value of the $^{32}$S(n,?)$^{33}$S, 8.641 MeV, reaction, while the second window corresponds to an energy of 7.800 MeV. FIG. 22 shows the results of projecting the whole spectrum to the x-axis, i.e. the total coincidence spectrum in the 5"×5" NaI detector in coincidence with all events in the 6"×6" NaI detector.

Figure 23:
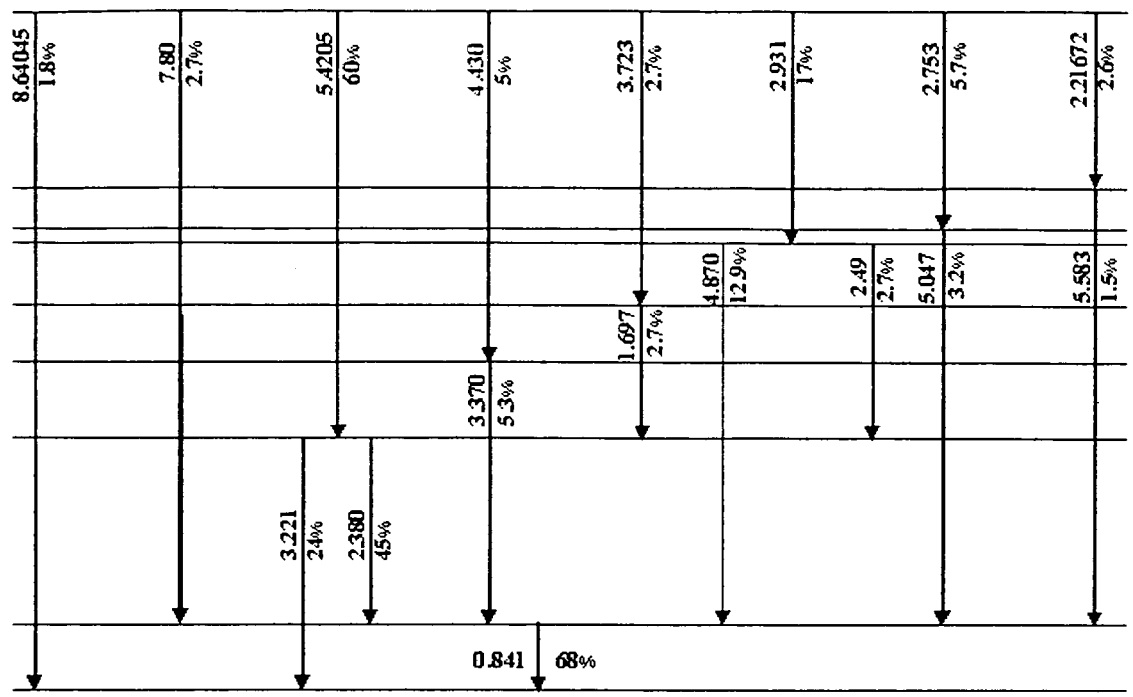
FIG. 23 is a Sulfur-33 gamma ray decay diagram according to embodiments of the present invention.
Figure 24:
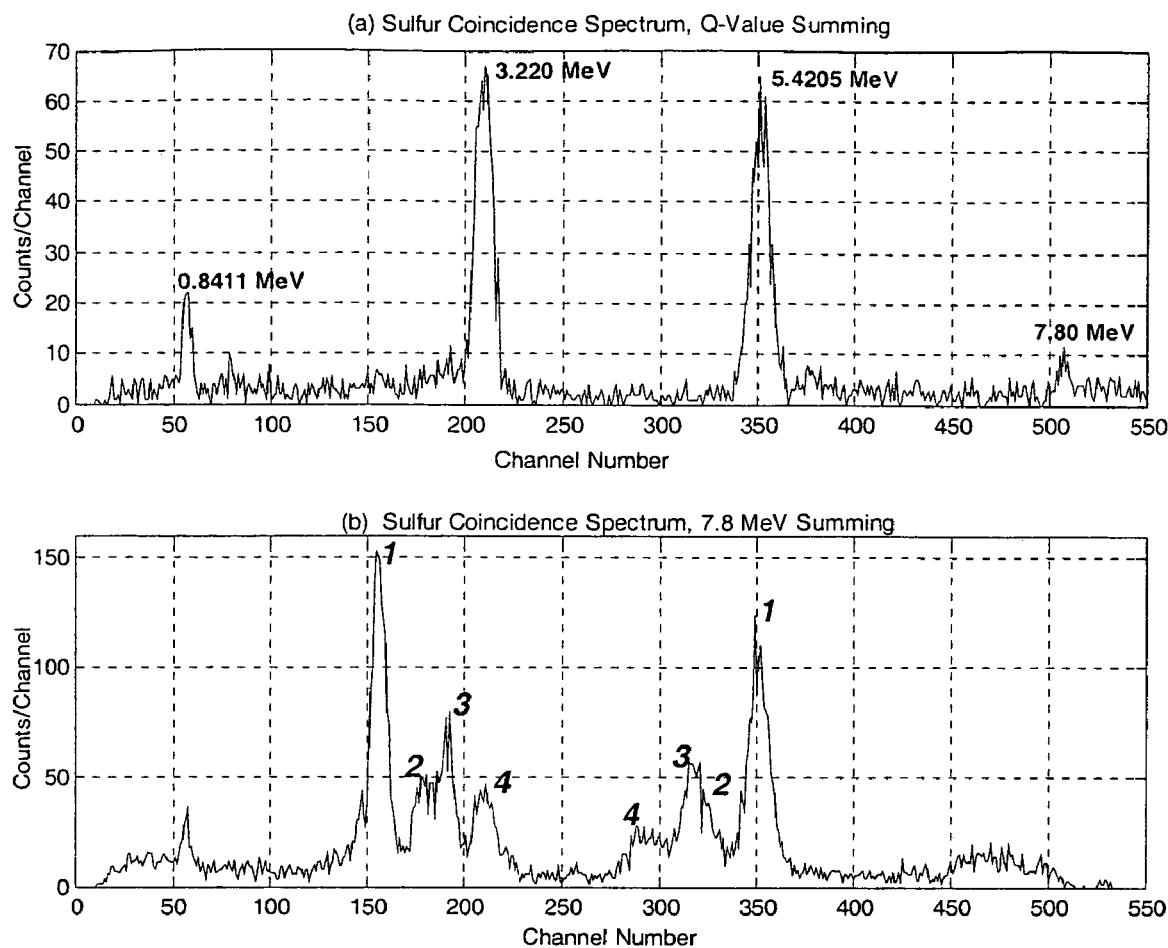
FIG. 24 is a graph illustrating the Q-value summing spectrum and the 7.8 MeV coincidence spectrum for sulfur according to embodiments of the present invention.
Figure 25:
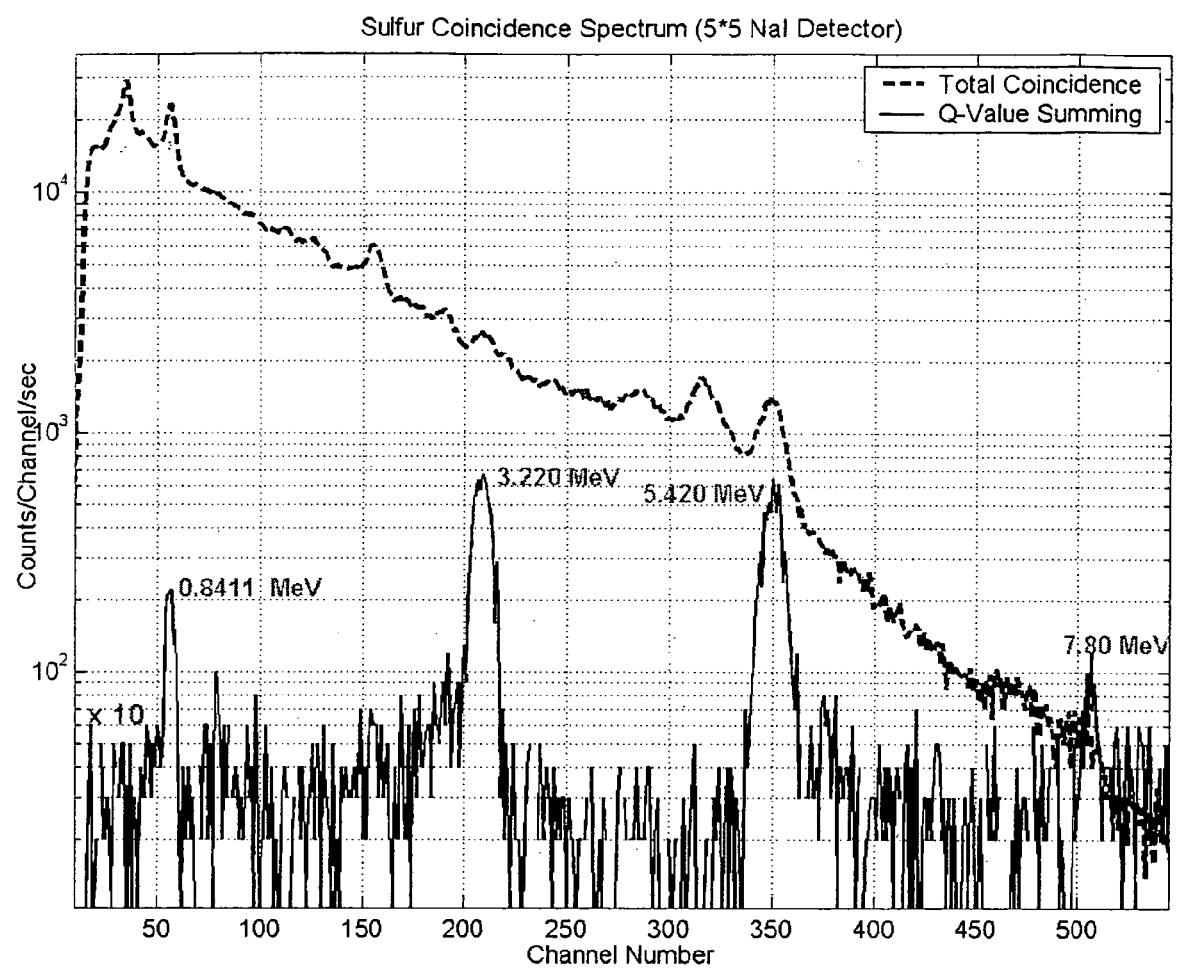
FIG. 25 is a graph illustrating a comparison between the total coincidence spectrum and the Q-value diagonal sum spectrum for sulfur according to embodiments of the present invention.
Figure 26:
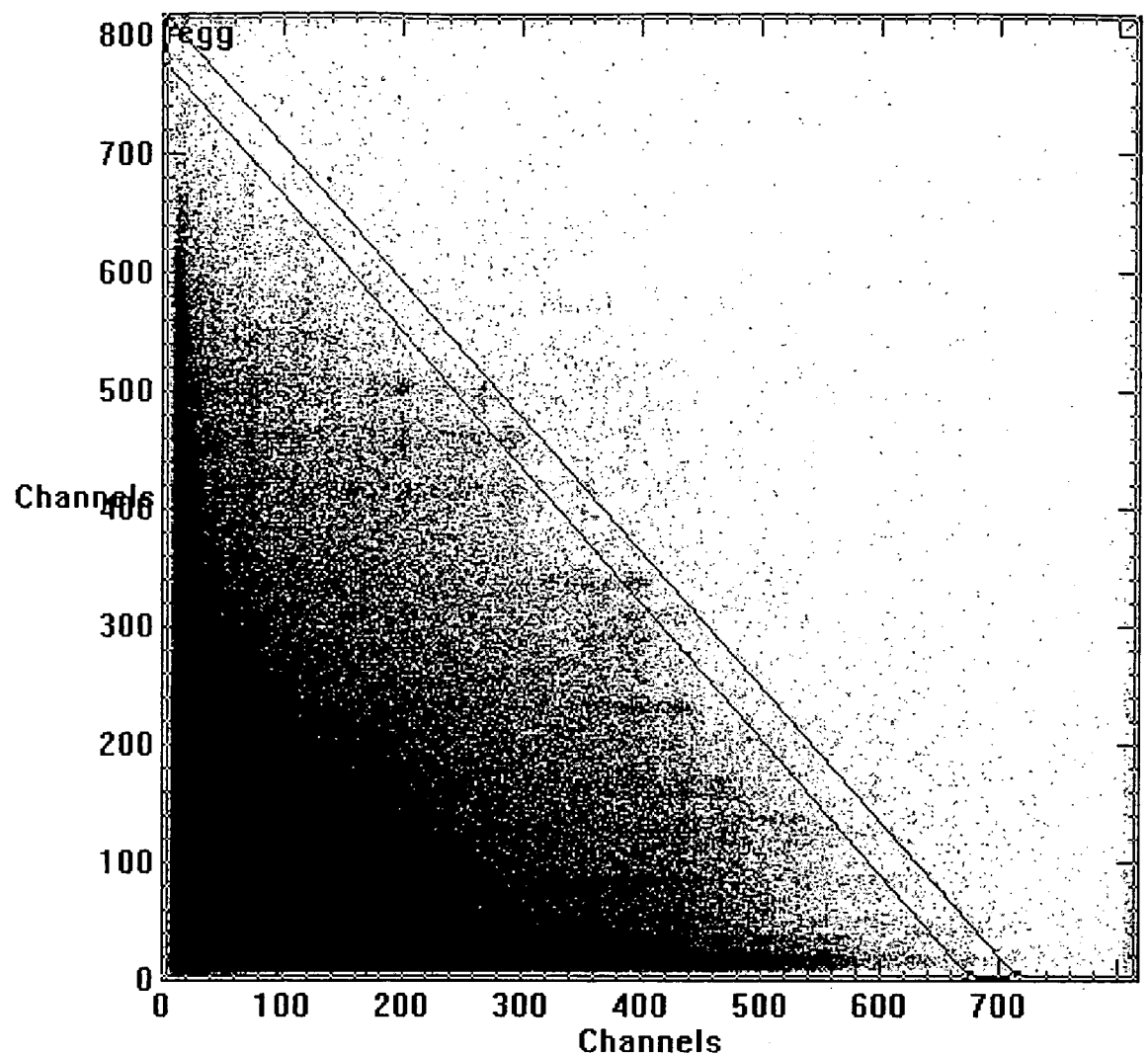
FIG. 26 is graph of a two-dimensional plot (flat view) of the event counts in two NaI detectors for a coal sample according to embodiments of the present invention.

The level scheme that can be used to analyze this data is shown in FIG. 26 along with the gamma intensities and energies (in MeV). This scheme accounts for approximately 93% of the transitions in the $^{33}$S decay. FIG. 24 shows the projection of Window 1 and Window 2 in FIG. 1 respectively. The energy of Window 1 corresponds to the Q-value of the $^{32}$S(n,?)$^{33}$S while that of Window 2 corresponds to 7.800 MeV. The energies of the schemes are 7.800 and 0.841 MeV, and 5.20 and 3.221 MeV. Thus, these four gamma rays may be visible when performing Q-value diagonal summing. (See FIG. 24). The 5.420–3.221 MeV pair may be more intense than the 7.800–0.841 MeV pair. This may be attributed to the difference in scheme probability. As illustrated in FIG. 23, several energies sum to 7.800 MeV. These energies are labeled on FIG. 24 as pair numbers 1 through 4. The energies corresponding to these pairs are listed in Table 5. FIG. 25 shows the Q-value diagonal summing spectrum compared with the total coincidence spectrum.

Figure 27:
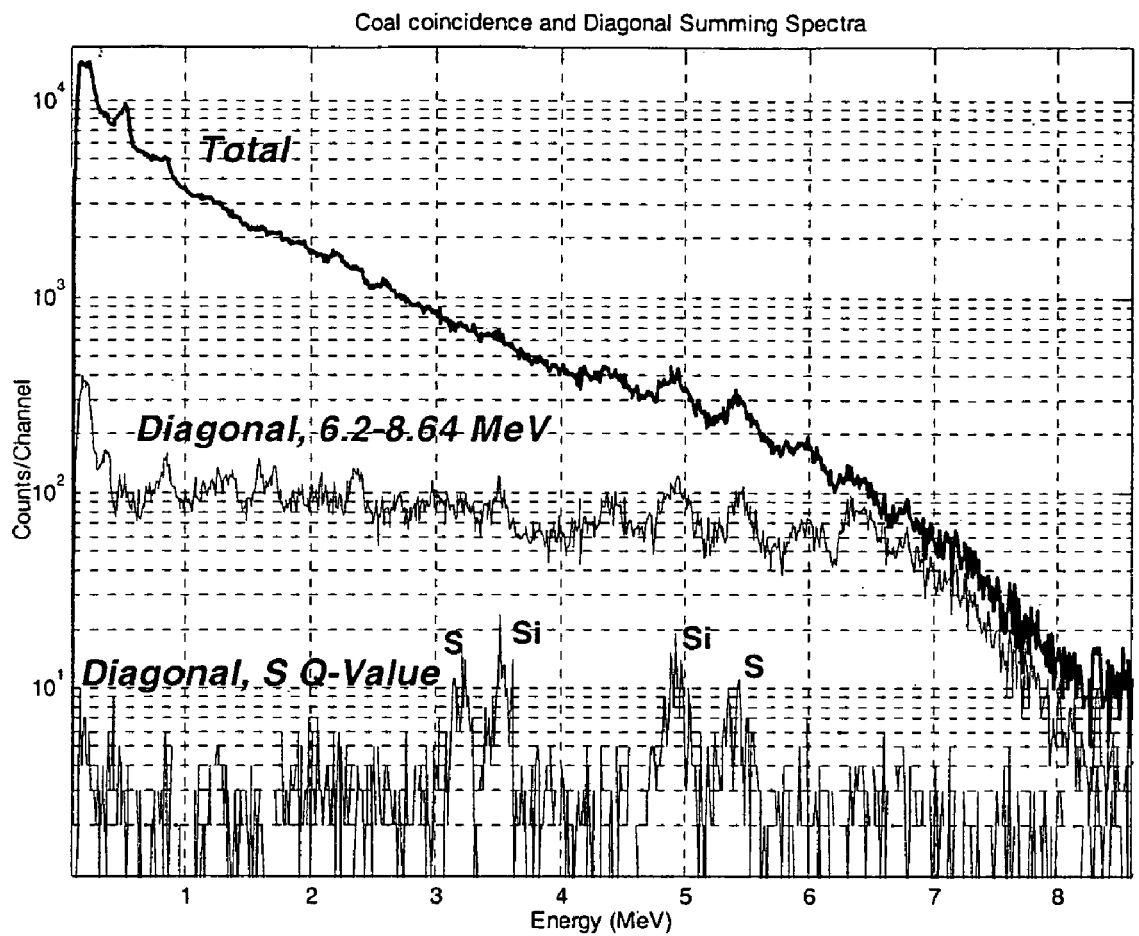
FIG. 27 is a graph illustrating a comparison of a full and diagonal summing spectra for a coal sample according to embodiments of the present invention.

FIG. 26 is a two-dimensional plot for a coal sample using the same detector configuration. As illustrated in FIG. 27, another diagonal summing spectrum can be isolated corresponding to an energy window from 6.200 MeV to 8.700 MeV. Summing over a range of high energies may reduce or eliminate the coincidences of interfering low energy gamma-ray pairs, thus increasing signal-to-noise (S/N) ratio.

EXAMPLE 9

Nickel

The NSCU PULSTAR thermal neutron beam was utilized in this experiment. The two NaI detectors (5"×5" and 6"×6") were positioned facing each other and the sample was positioned between the detectors. The sample-to-detector distance was 20 cm. The sample was elemental natural nickel.

Figure 28:
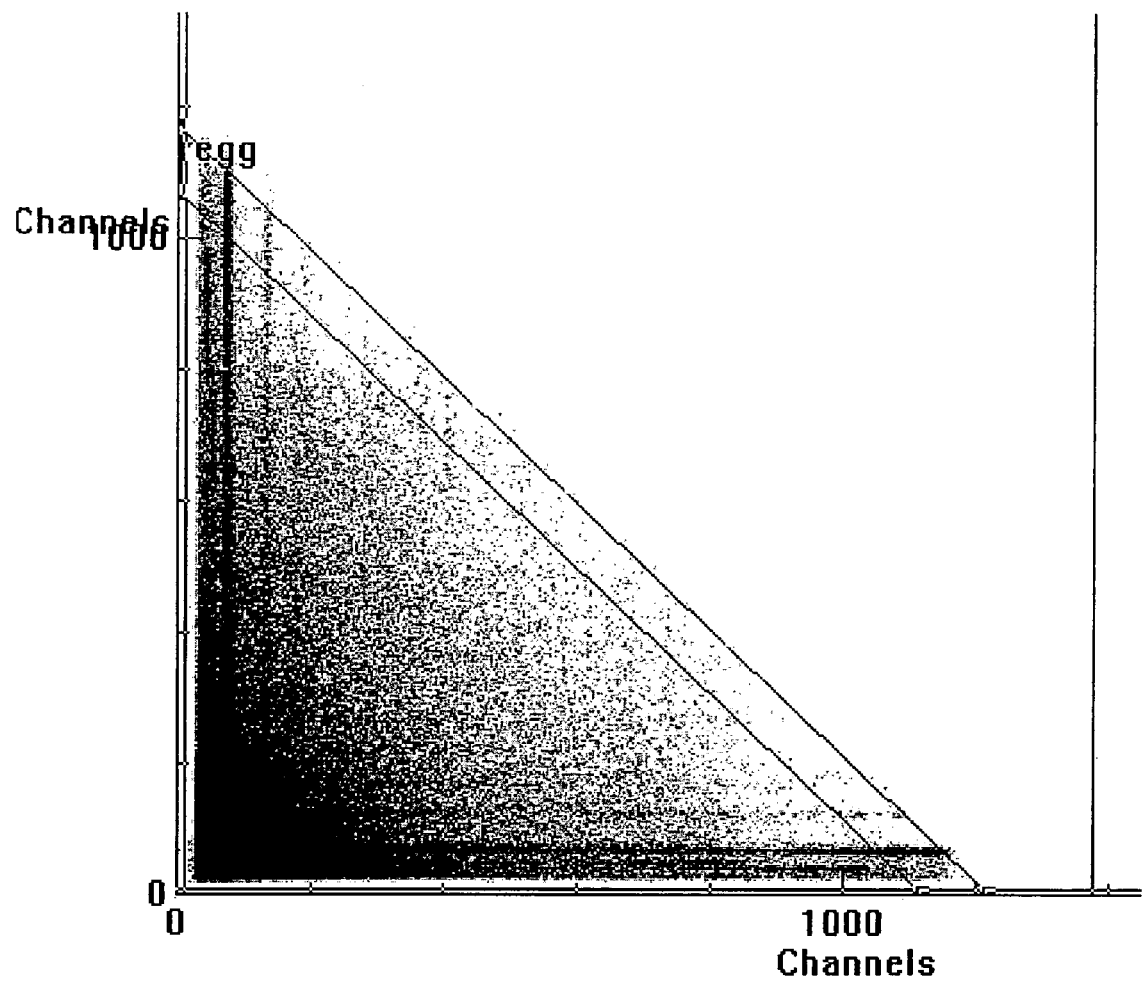
FIG. 28 is a graph of a two-dimensional plot (flat view) of the event counts of two NaI detectors for a nickel sample according to embodiments of the present invention.
Figure 29:
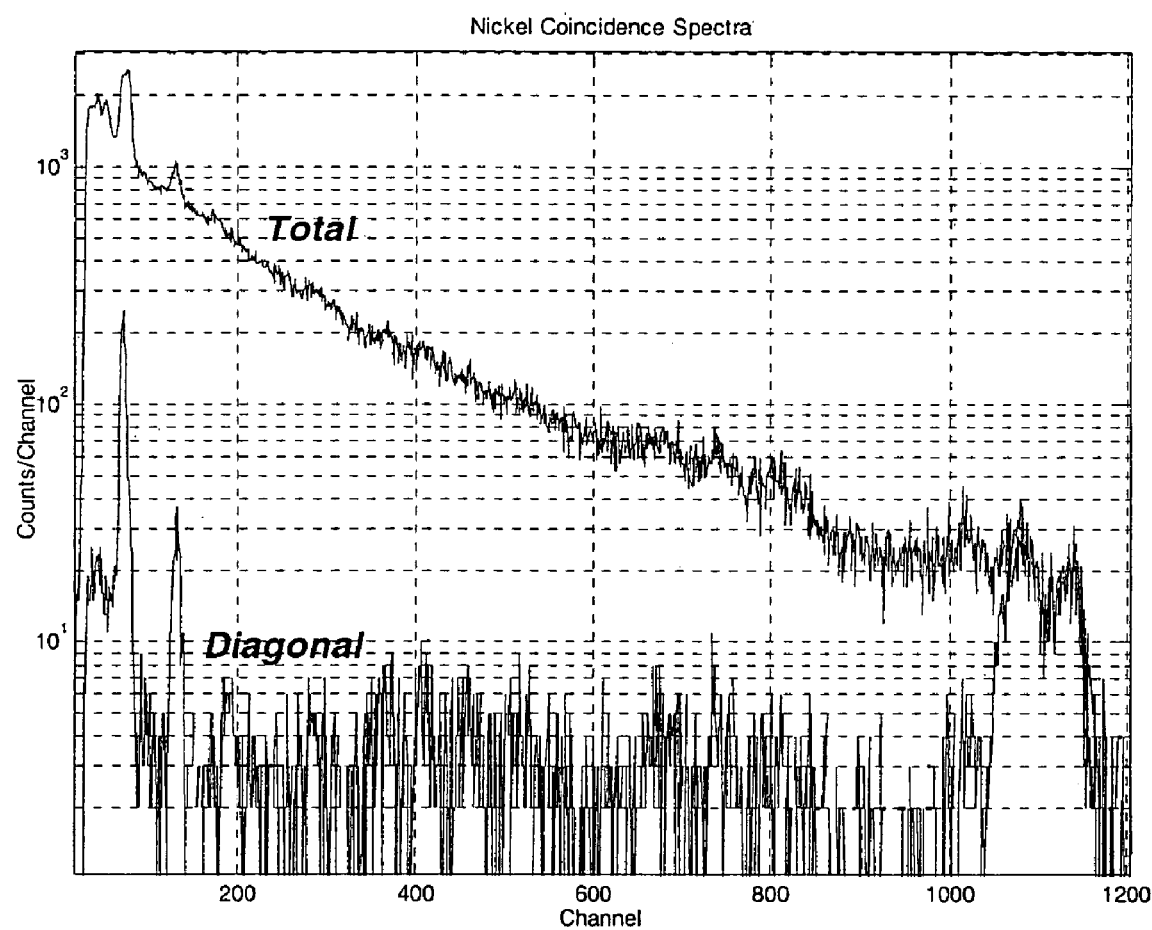
FIG. 29 is a graph illustrating a comparison of the full and the diagonal summing spectra for a nickel sample according to embodiments of the present invention.
Figure 30:
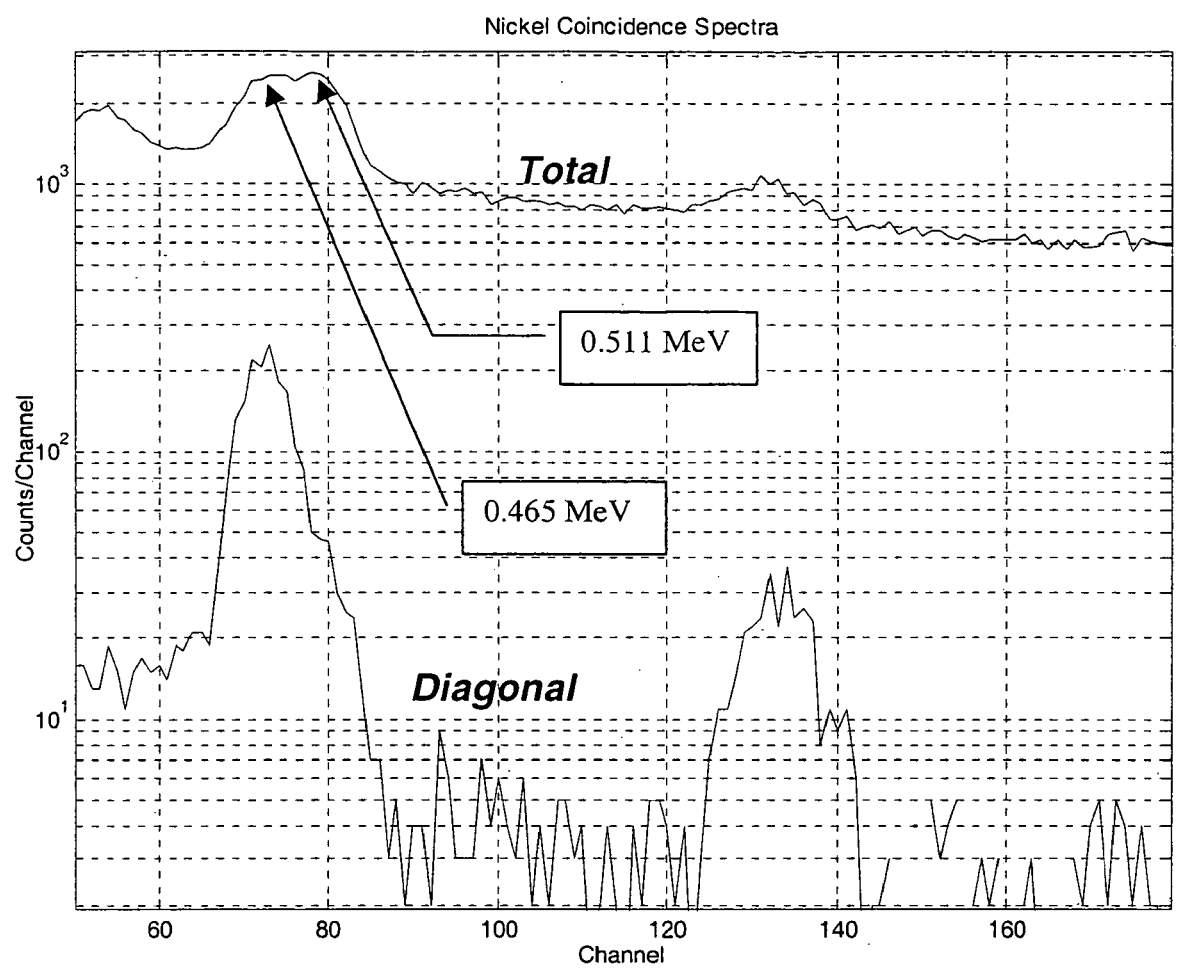
FIG. 30 is a graph illustrating a comparison between the full and the diagonal summing spectra for nickel in the 0.511 MeV energy range according to embodiments of the present invention.
Figure 31:
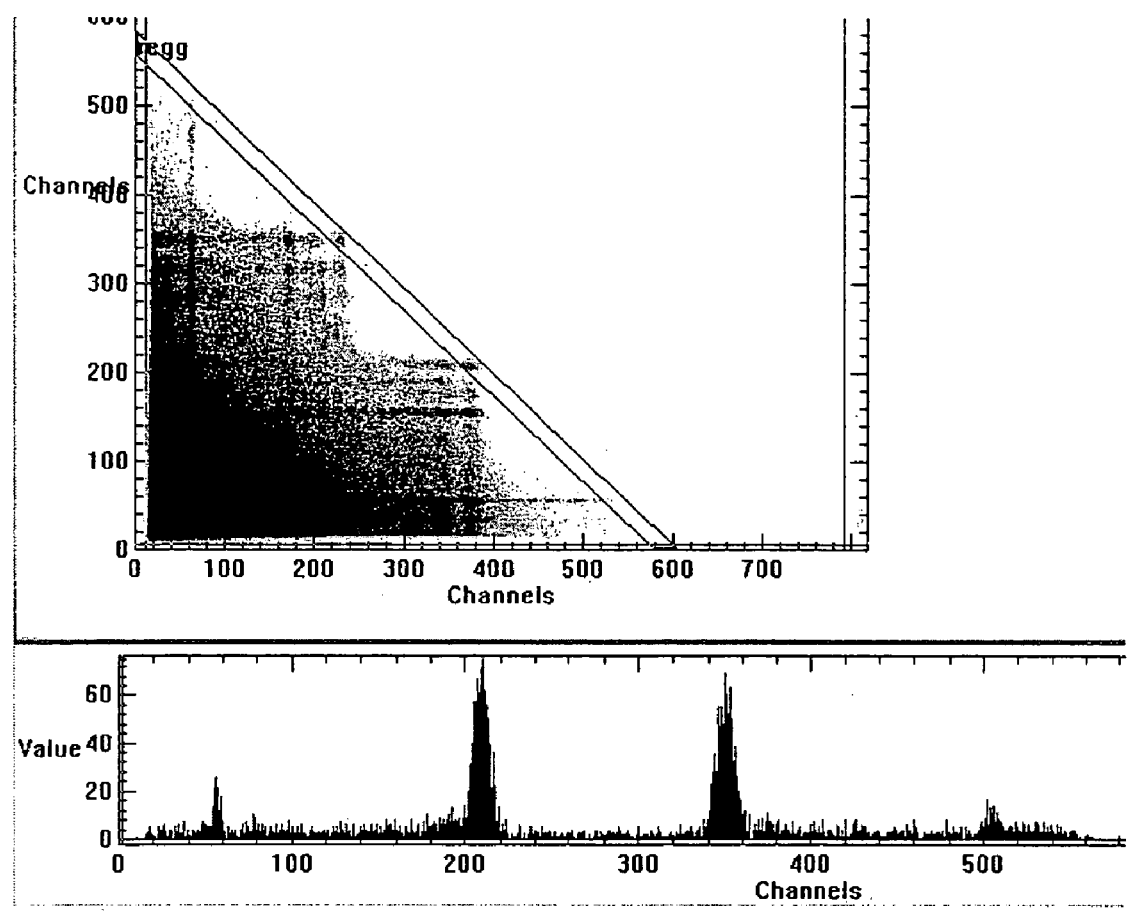
FIG. 31–35 are graphs illustrating a two-dimensional plot for a sulfur sample and a diagonal summing spectra corresponding to scans 1–5, respectively, according to embodiments of the present invention.
Figure 32:
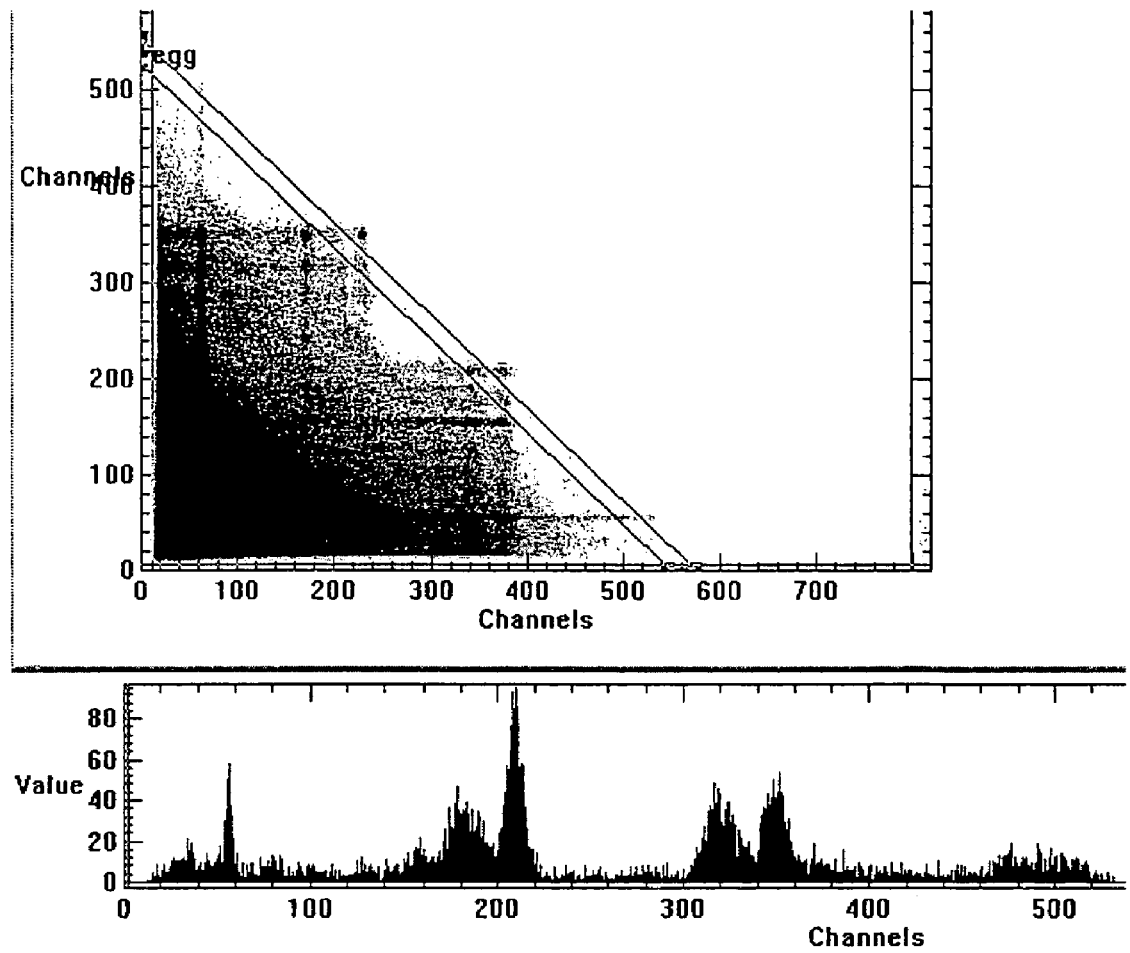
Figure 33:
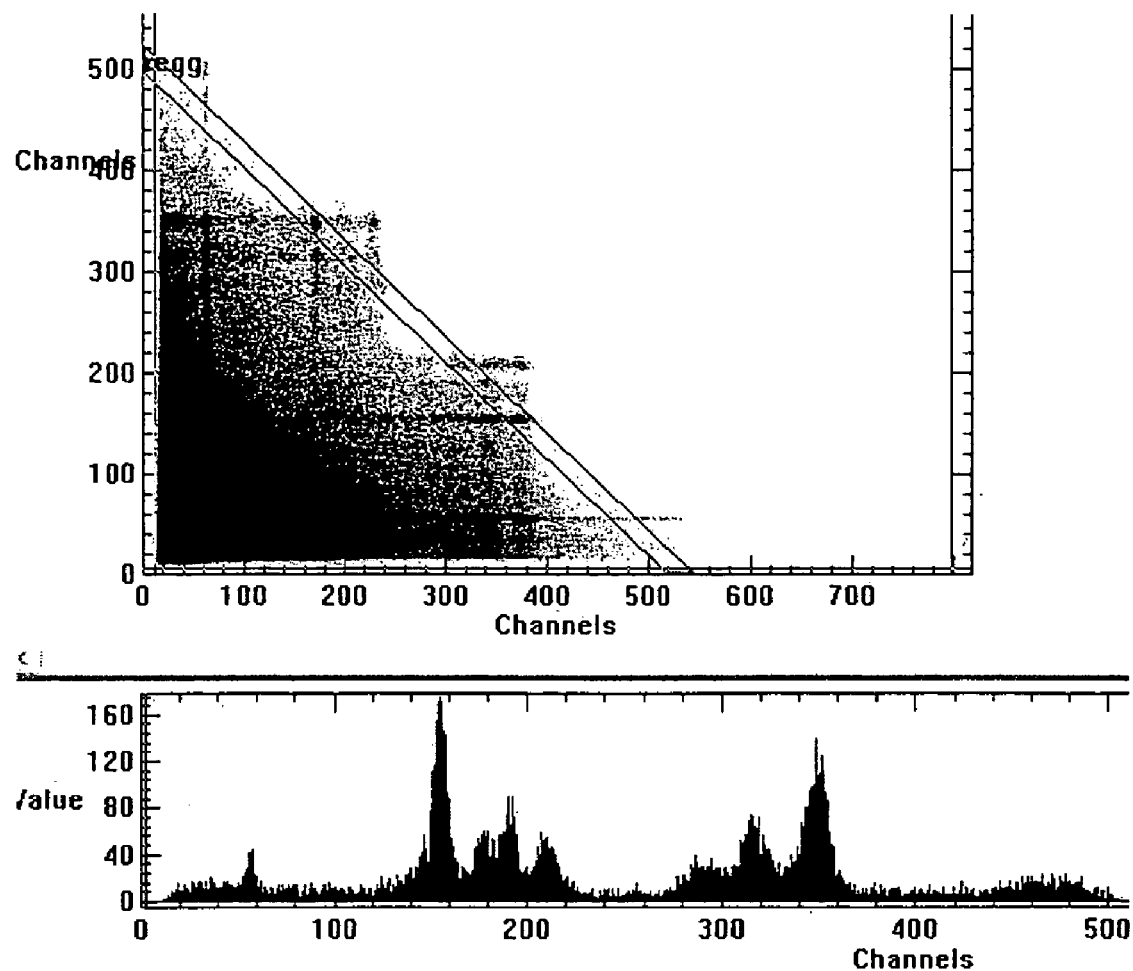
Figure 34:
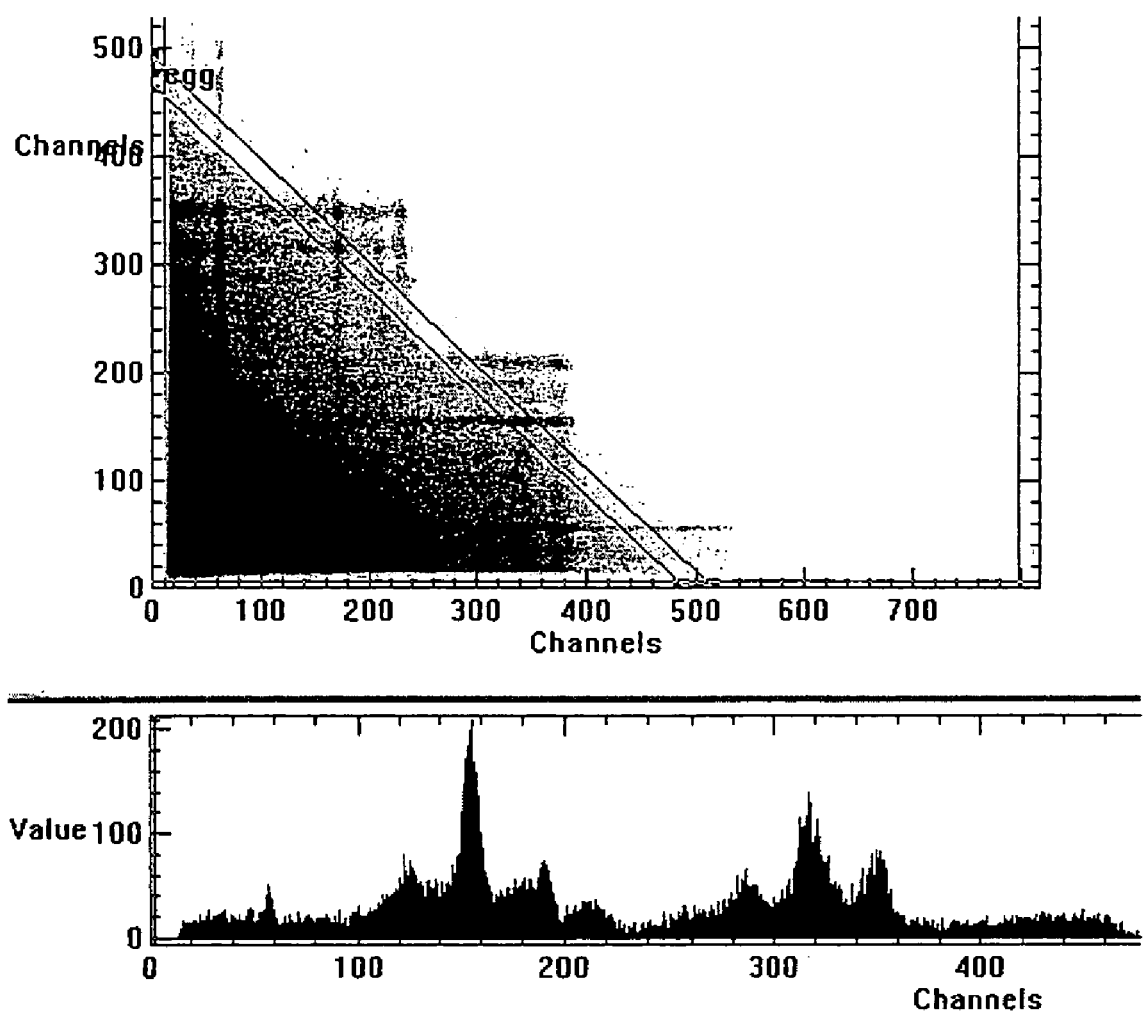
Figure 35:
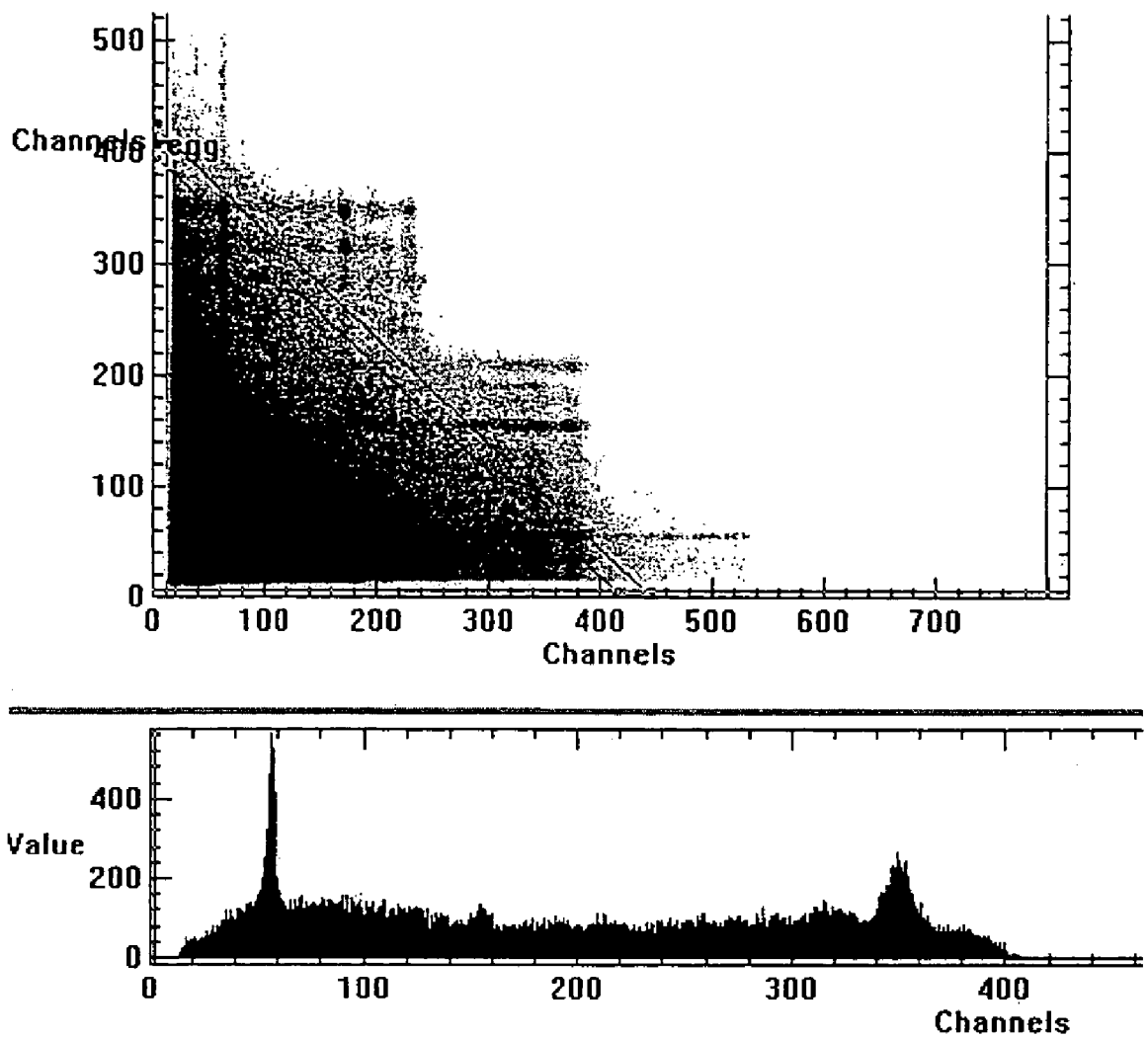
Figure 36:
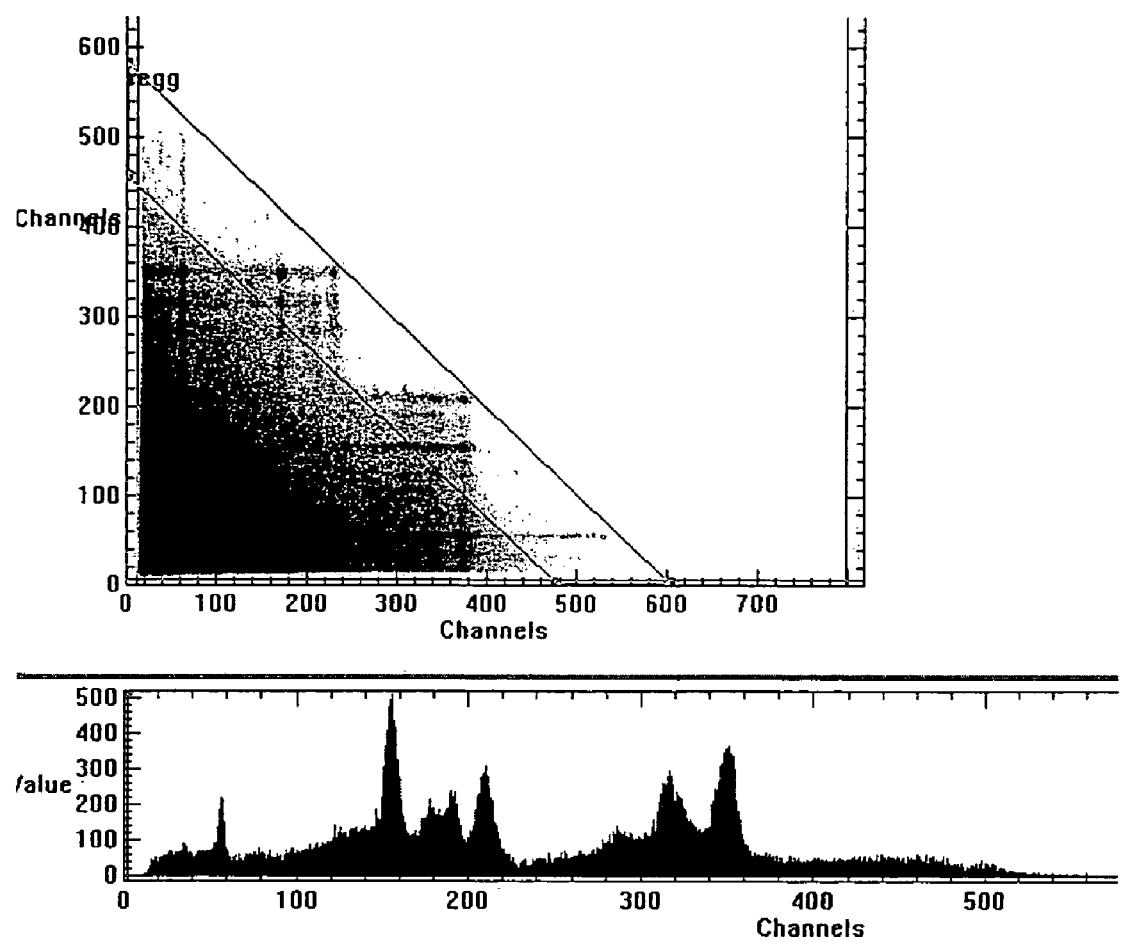
FIGS. 36–38 are graphs illustrating two-dimensional plots for a sulfur sample and various diagonal summing windows according to embodiments of the present invention.
Figure 37:
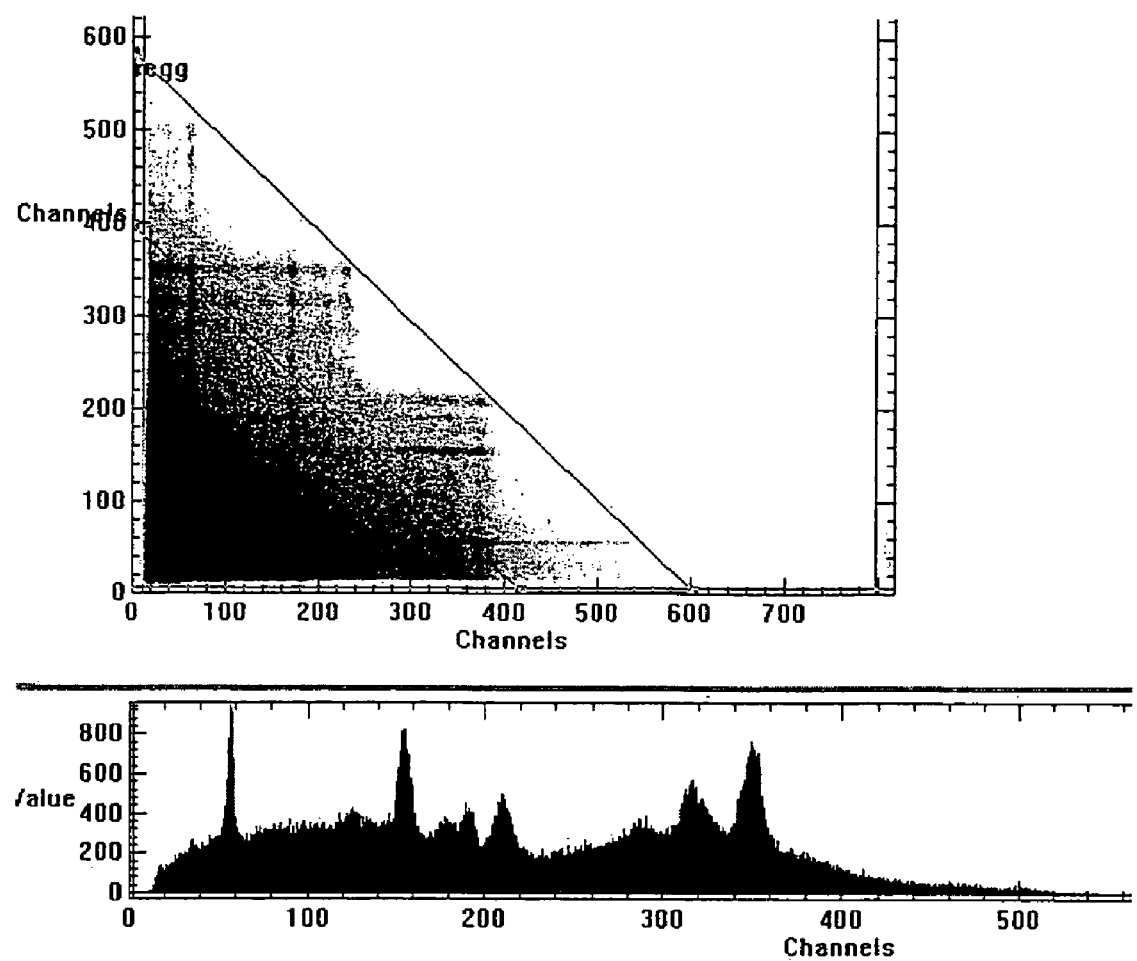
Figure 38:
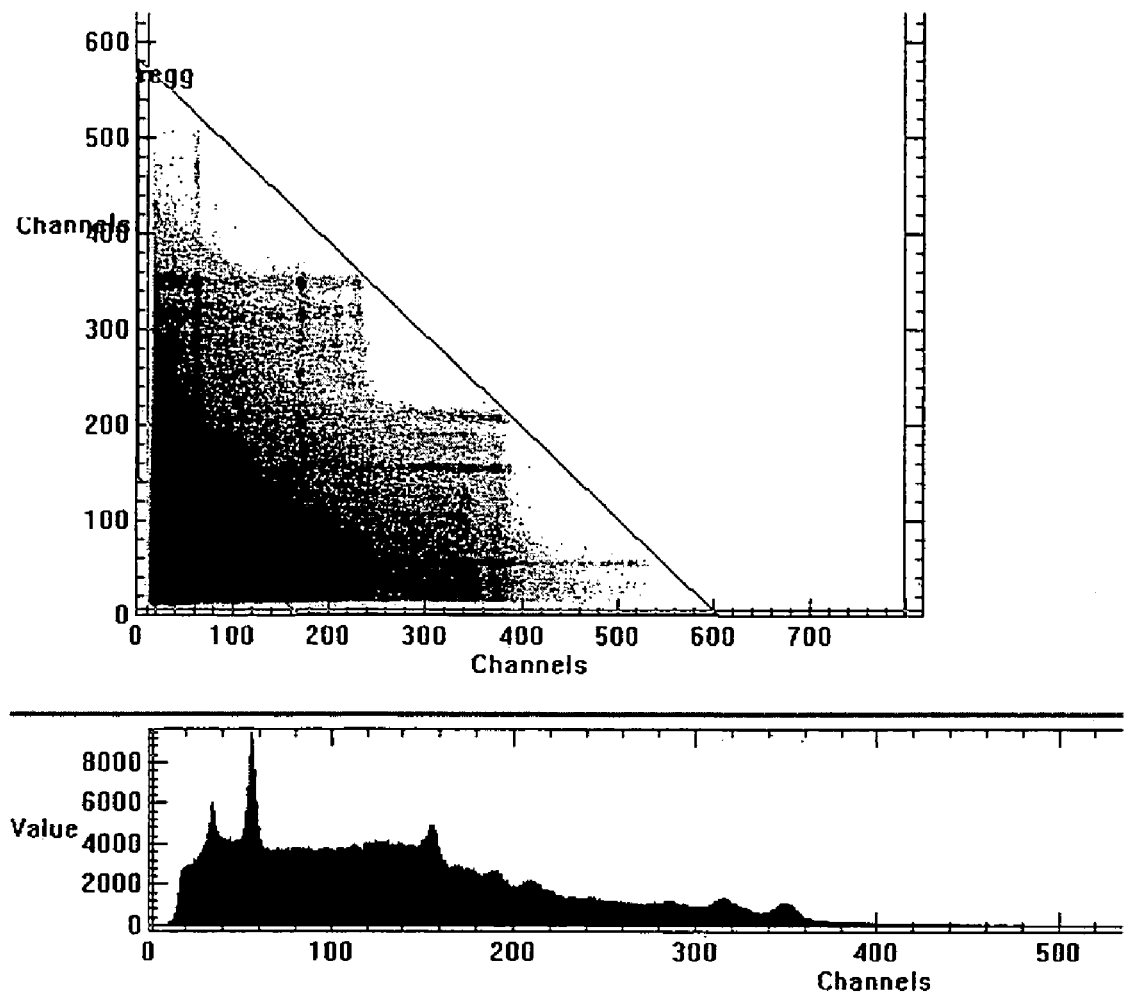

FIG. 28 shows the two-dimensional plot (flat view) of the counts in both NaI detectors. The outlined diagonal window corresponds to the Q-value of the $^{58}$Ni(n,?)$^{59}$Ni reaction, 8.998 MeV, which is the dominant (n,?) interaction with natural nickel. FIG. 29 illustrates the Q-value diagonal summing spectrum for natural nickel compared with the total coincidence spectrum. FIG. 30 shows an expanded view of the FIG. 29 in the low energy range. It can be seen that the diagonal summing approach can result in the substantial elimination of the 0.511 MeV peak from the spectrum.

EXAMPLE 10

Scanning Approaches, Window Selection and the Least Squares Approach

A fixed diagonal energy window width was used. The two-dimensional spectra were scanned and the resulting spectra were observed. The spectra obtained from various scans using the data from Example 8 is illustrated in FIGS. 31–35.

Figure 39:
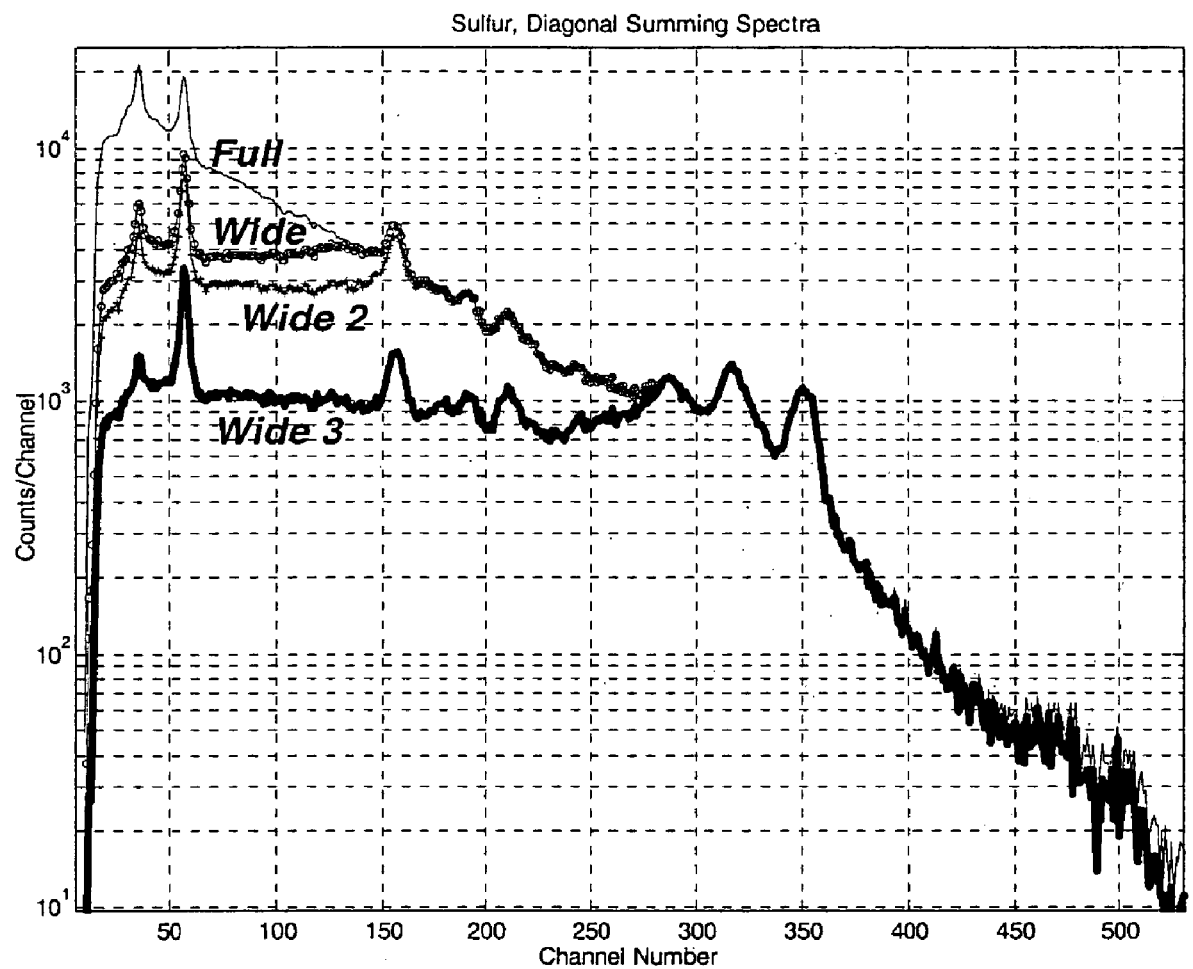
FIG. 39 is a graph illustrating a comparison of a full and diagonal summing spectra for sulfur for variable energy widow.

A fixed upper value of the diagonal energy window was selected and the width of the windows varied. FIGS. 36–39 show the results of this process using data from Example 4. FIG. 39 shows the diagonal summing spectrum at different energy widths compared with the total coincidence spectrum. Summing over a range of high energies reduces or eliminates the coincidences of interfering low energy gamma-ray pairs, thus increasing signal-to-noise (S/N) ratio.

The diagonal summing spectra presented in FIG. 39 are examples of where the Library Least Squares (LLS) approach can be applied. The LLS approach is useful for inverse spectral problems such as determining elemental amounts from gamma-ray, X-ray or prompt gamma-ray spectra. The diagonal summing spectra from either a narrow or a wide window, such as those in FIG. 39 may be used with the LLS approach. The optimum diagonal window width can depend on the specific application and/or element of interest.

Other analysis and calculation techniques can be used, including Monte Carlo simulations.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. An assembly for detecting gamma rays from a bulk material, the assembly defining a radiation region, the assembly comprising:
   a radiation source adjacent the radiation region configured to irradiate the bulk material in the radiation region;
   a first gamma ray detector positioned adjacent the radiation region and configured to detect gamma ray events including events from gamma rays secondarily emitted by the bulk material responsive to radiation from the radiation source;
   a second gamma ray detector positioned adjacent the first gamma ray detector and configured to detect gamma ray events including events from gamma rays secondarily emitted by the bulk material responsive to radiation from the radiation source;
   a gamma ray shielding material between the first and second gamma ray detectors; and
   a coincidence module configured to receive signals indicating gamma ray events from each of the first and second gamma ray detectors and to identify events that are detected in coincidence in the first and second gamma ray detectors and to generate a two-dimensional plot based on the signals from the first and second gamma ray detectors.

2. The assembly of claim 1, wherein the second gamma ray detector comprises an array of gamma ray detectors, each of the gamma ray detectors in the array configured to provide respective signals indicating gamma ray events.

3. The assembly of claim 1, further comprising a first photomultiplier tube in communication with the first gamma ray detector and a second photomultiplier tube in communication with the second gamma ray detector.

4. The assembly of claim 1, wherein the coincidence module is configured to determine coincidence counting rates between the first and second gamma ray detectors.

5. The assembly of claim 4, wherein the coincidence counting rate is the total rate of coincidence between the first and second gamma ray detectors.

6. The assembly of claim 4, wherein the coincidence module is configured to select a subset of the events from one of the first and second detectors and to identify gamma ray events in the other of the first and second detectors in coincidence with the selected subset.

7. The assembly of claim 4, wherein the coincidence counting rate is the rate of coincidence between a first event and a second event, wherein the first event and the second event sum to a predetermined energy.

8. The assembly of claim 7, wherein the predetermined energy is between about 1.5 MeV to about 11 MeV.

9. The assembly of claim 1, wherein the coincidence module is configured to generate a one-dimensional diagonal summation plot based on the two-dimensional plot.

10. The assembly of claim 1, further comprising a conveyor belt configured to transport the bulk material through the radiation region.

11. The assembly of claim 1, further comprising a chute configured to continually transport the bulk material through the radiation region.

12. A method of detecting coincidence in gamma ray detectors for analyzing a bulk material comprising:
    providing the bulk material in a radiation region;
    irradiating the bulk material in the radiation region with a radiation source adjacent the radiation region;
    detecting gamma ray events with a first gamma ray detector adjacent the radiation region, the gamma ray events including events from gamma rays secondarily emitted by the bulk material responsive to radiation from the radiation source;
    detecting gamma ray events with a second gamma ray detector adjacent the first gamma ray detector, the gamma ray events including events from gamma rays secondarily emitted by the bulk material responsive to radiation from the radiation source;
    shielding gamma rays between the first and second gamma ray detectors;
    identifying gamma ray events that are detected in coincidence in the first and the second gamma ray detectors; and
    generating a two-dimensional plot based on the signals from the first and second gamma ray detectors.

13. The method of claim 12, wherein the second gamma ray detector comprises an array of gamma ray detectors.

14. The method of claim 12, wherein identifying gamma ray events comprises determining a coincidence counting rate between the first and second gamma ray detectors.

15. The method of claim 14, wherein the coincidence counting rate is the total rate of coincidence between the first and second gamma ray detectors.

16. The method of claim 14, wherein determining a coincidence counting rate comprises selecting a subset of the events from one of the first and second detectors and identifying gamma ray events in the other of the first and second detectors in coincidence with the selected subset.

17. The method of claim 14, wherein the coincidence counting rate is the rate of coincidence between a first event and a second event, wherein the first event and the second event sum to a predetermined energy.

18. The method of claim 17, wherein the predetermined energy is between about 1.5 MeV to about 11 MeV.

19. The method of claim 12, further comprising generating a one-dimensional diagonal summation plot based on the two-dimensional plot.

20. The method of claim 12, wherein providing the bulk material includes transporting the bulk material through the radiation region using a conveyor belt.

21. The method of claim 12, wherein providing the bulk material includes passing the bulk material through the radiation region using a chute.

* * * * *